US009758834B2

(12) United States Patent
Webster et al.

(10) Patent No.: US 9,758,834 B2
(45) Date of Patent: Sep. 12, 2017

(54) COMPOSITIONS AND METHODS FOR DIAGNOSING CANCER

(75) Inventors: Philippa Jane Webster, Seattle, WA (US); Richard Kemble Boykin, Shoreline, WA (US); Jeannette Nussbaum, Seattle, WA (US)

(73) Assignee: NanoString Technologies, Inc., Seattle, WA (US)

( * ) Notice: Subject to any disclaimer, the term of this patent is extended or adjusted under 35 U.S.C. 154(b) by 0 days.

(21) Appl. No.: 14/007,586

(22) PCT Filed: Mar. 28, 2012

(86) PCT No.: PCT/US2012/030940
§ 371 (c)(1),
(2), (4) Date: Sep. 25, 2013

(87) PCT Pub. No.: WO2012/135340
PCT Pub. Date: Oct. 4, 2012

(65) Prior Publication Data
US 2014/0017688 A1   Jan. 16, 2014

Related U.S. Application Data

(60) Provisional application No. 61/468,361, filed on Mar. 28, 2011.

(51) Int. Cl.
*C07H 21/04* (2006.01)
*C12Q 1/68* (2006.01)

(52) U.S. Cl.
CPC ...... *C12Q 1/6886* (2013.01); *C12Q 2600/112* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| 5,320,814 | A | 6/1994 | Walt et al. |
| 5,543,838 | A | 8/1996 | Hosier et al. |
| 6,207,392 | B1 | 3/2001 | Weiss et al. |
| 6,429,027 | B1 | 8/2002 | Chee et al. |
| 6,576,421 | B1 | 6/2003 | Westbrook |
| 6,942,968 | B1 | 9/2005 | Dickinson et al. |
| 8,519,115 | B2 * | 8/2013 | Webster et al. ............ 536/24.3 |
| 9,046,477 | B2 | 6/2015 | Emedcoles et al. |
| 9,228,948 | B2 | 1/2016 | Emedcoles et al. |
| 9,297,762 | B2 | 3/2016 | Emedcoles et al. |
| 9,304,084 | B2 | 4/2016 | Emedcoles et al. |

| 2001/0002315 | A1 | 5/2001 | Schultz et al. |
| 2001/0007775 | A1 | 7/2001 | Seul et al. |
| 2001/0023078 | A1 | 9/2001 | Bawendi et al. |
| 2001/0029049 | A1 | 10/2001 | Walt et al. |
| 2001/0034034 | A1 | 10/2001 | Bruchez et al. |
| 2001/0053334 | A1 | 12/2001 | Chen et al. |
| 2002/0028457 | A1 | 3/2002 | Empedocles et al. |
| 2002/0034737 | A1 | 3/2002 | Drmanac |
| 2002/0034827 | A1 | 3/2002 | Singh et al. |
| 2002/0039728 | A1 | 4/2002 | Kain et al. |
| 2002/0051971 | A1 | 5/2002 | Stuelpnagel et al. |
| 2002/0055109 | A1 * | 5/2002 | Thill ................................. 435/6 |
| 2002/0068018 | A1 | 6/2002 | Pepper et al. |
| 2002/0177141 | A1 | 11/2002 | Chee et al. |
| 2002/0187515 | A1 | 12/2002 | Chee et al. |
| 2003/0008323 | A1 | 1/2003 | Ravkin et al. |
| 2003/0028981 | A1 | 2/2003 | Chandler et al. |
| 2003/0099987 | A1 | 5/2003 | Westbrook |
| 2003/0186426 | A1 | 10/2003 | Brewer et al. |
| 2004/0235039 | A1 | 11/2004 | Gray et al. |
| 2005/0233318 | A1 | 10/2005 | Chee et al. |
| 2006/0134667 | A1 | 6/2006 | Narahara et al. |
| 2010/0047924 | A1 | 2/2010 | Webster et al. |
| 2011/0319283 | A1 * | 12/2011 | Thompson ............ C12Q 1/6816 506/9 |

FOREIGN PATENT DOCUMENTS

| WO | WO-9707245 | 2/1997 |
| WO | WO-9714028 | 4/1997 |
| WO | WO-9918434 | 4/1999 |
| WO | WO-0073777 | 12/2000 |
| WO | WO-0100875 | 1/2001 |
| WO | 2007076128 | * 7/2007 ............... C12Q 1/68 |
| WO | WO-2010/039275 A1 | 4/2010 |

OTHER PUBLICATIONS

Kreuzer et al. (Cancer Research, vol. 59, pp. 3171-3174, Jul. 1999).*
Alfano et al., "Optical Sensing, Imaging,and Manipulation for Biological and biomedical applications" SPIE—The International Society for Optical Engineering, Jul. 2000, vol. 4082, Taiwan.
Ferguson et al., "High-Density Fiber-Optic DNA Random Microsphere Array" *Analytical Chemistry* 72 (22), 5618-5624 (2000).
Steemers et al., "Screening unlabeled DNA targets with randomly ordered fiber-optic gene arrays." *Nature Biotechnology.* 18, 91-94 (2000).
Werner et al., "Current status of DNA sequencing by single molecule detection" Proc. SPIE 3602, Advances in Fluorescence Sensing Technology IV, 355, (1999).

* cited by examiner

*Primary Examiner* — Jeanine A Goldberg
(74) *Attorney, Agent, or Firm* — Cooley LLP; Ivor R. Elrifi; Matthew Pavao

(57) ABSTRACT

The application describes methods for diagnosing subjects with leukemia by detecting fusion genes associated with the onset of leukemia.

12 Claims, 5 Drawing Sheets

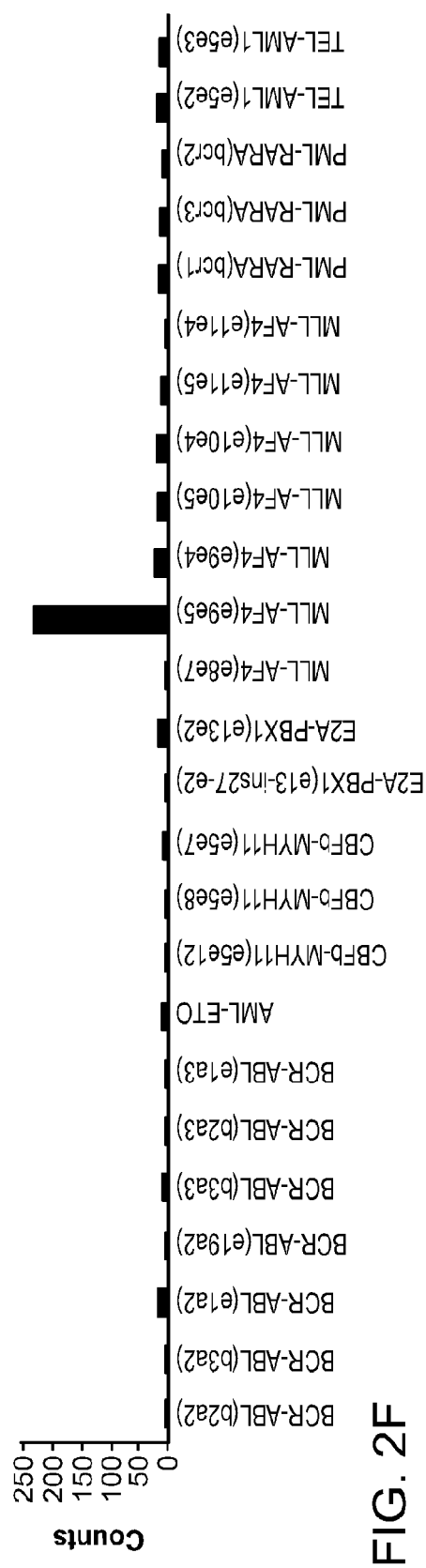

COMPOSITIONS AND METHODS FOR DIAGNOSING CANCER

CROSS-REFERENCE TO RELATED APPLICATIONS

This application is a national stage application, filed under 35 U.S.C. §371, of International Application No. PCT/US2012/030940, filed on Mar. 28, 2012, which claims the benefit of provisional applications U.S. Ser. No. 61/468,361 filed Mar. 28, 2011, the contents which are each herein incorporated by reference in their entirety.

SEQUENCE LISTING

The Sequence Listing associated with this application is provided in text format in lieu of a paper copy, and is hereby incorporated by reference into the specification. The name of the text file containing the Sequence Listing is NATE-011-NO1US SEQ LISTING.txt. The text file is 36 KB, was created on Dec. 10, 2015, and is being submitted electronically via EFS-Web.

FIELD OF THE INVENTION

This disclosure relates generally to the field of cancer biology, and specifically, to the fields of detection and identification of specific cancer cell phenotypes and correlation with relevant patient prognosis.

BACKGROUND OF THE INVENTION

Recurrent chromosomal translocations characterize a substantial proportion of leukemias, resulting in the formation of unique fusion genes. The identification of particular fusion gene abnormalities is of considerable diagnostic and prognostic importance. There is a need in the art for reliable diagnostic compositions for the detection and diagnosis of leukemias and sub-types of leukemias based on gene fusion.

SUMMARY OF THE INVENTION

Leukemia is often accompanied by the formation of fusion genes. These chromosomal abnormalities are caused by the reciprocal translocation of portions of genes at different chromosomal locations forming a new gene characterized by the fusion of a nucleic acid sequence from a first and a second gene. For example, the BCR-ABL fusion gene is caused by a reciprocal translocation of parts of chromosome 9 and 22. Specifically, the translocated regions are 9p34 and 22q11. This joins a portion of the ABLI gene on chromosome 9 to a part of the BCR ("breakpoint cluster region") of chromosome 22. The presence of this and other fusion genes is correlated with the onset and progression of various types of leukemia. This disclosure presents compositions and methods for the diagnosis and prognosis of leukemia based on the detection of fusion genes.

The disclosure provides a composition for the diagnosis of leukemia. In one embodiment, this composition includes one or more target-specific nucleic acid probes. Each of the one or more target-specific probes includes a target-specific region that specifically binds to one target nucleic acid analyte; and a region to which is attached a plurality of label monomers that create a unique label for each target-specific probe. The label has a detectable signal that distinguishes one target-specific probe which binds to a first target nucleic acid from another target-specific probe that binds to a different second target nucleic acid. One or more targets of the one or more target-specific probes include a fusion gene or mRNA transcribed from said fusion gene. The fusion gene is the result of the fusion of two or more genes in a patient at the onset of or during progression of leukemia.

The fusion genes can be caused by the fusion of two or more genes at the onset of leukemia. The fusion gene can be BCR-ABL, AML-ETO, CBFB-MYH11, E2A-PBX1, MLL-AF4, PML-RARA, or TEL-AML1. The fusions can be between varying exons of the upstream and downstream genes. The leukemia can be chronic myelogenous leukemia, acute myeloid leukemia or acute lymphoblastic leukemia.

In certain embodiments, at least one of the one or more target-specific probes has a target that is the sequence of the junction where the two genes are fused. These target-specific probes can also include a target-specific region with one or more mismatches to the target of the target-specific region.

In other specific embodiments, the label monomers can be a fluorochrome moiety, a fluorescent moiety, a dye moiety or a chemiluminescent moiety. The unique label for each target-specific probe can be composed of 4 or 5 label monomers.

The disclosure also provides a composition for the diagnosis of leukemia and different sub-types of leukemia. In one embodiment, the composition comprises a probe pair including a first probe and a second probe. The first probe is made up, at least in part, of a complex including a first molecule. The first molecule includes a first label attachment region to which are attached one or more label monomers that emit light constituting a first signal. The first molecule also includes a second label attachment region, which is non-overlapping with the first label attachment region, to which are attached one or more label monomers that emit light constituting a second signal. The first molecule also includes a first target-specific sequence attached to the first molecule. The second probe is made up, at least in part, of a second molecule including a second target-specific sequence and an affinity tag. The first target-specific sequence and the second target-specific sequence bind to different regions of the same target molecule. The target molecule is a fusion gene or mRNA transcribed from said fusion gene. The fusion gene is the result of the fusion of two or more genes in a patient at the onset of or during progression of leukemia. Also, when said probe pair is bound to its target molecule, the identity of the first and second signals and their locations relative to each other constitute at least part of a code that identifies the target molecule.

In certain embodiments, the fusion gene results from the fusion of at least a portion of a first gene and at least a portion of a second gene. In this situation, the first target-specific sequence can hybridize to a portion of the first gene and the second target-specific sequence can hybridize to a portion of the second gene. The first target-specific sequence can hybridize to a sequence adjacent to a sequence that the second target-specific sequence hybridizes to on the fusion gene.

In other embodiments, the first target-specific sequence can also hybridize to a portion of the first gene and a portion of the second gene. In this situation, the first target-specific sequence can hybridize to a sequence adjacent to a sequence that the second target-specific sequence hybridizes to on the fusion gene. At least one of the target-specific sequences can include a region with one or more mismatches to the target of the target-specific sequence.

The second target-specific sequence can also hybridize to a portion of the first gene and a portion of the second gene.

In this situation, the first target-specific sequence can hybridize to a sequence adjacent to a sequence that the second target-specific sequence hybridizes to on the fusion gene. At least one of the target-specific sequences can include a region with one or more mismatches to the target of the target-specific sequence.

The leukemia can be chronic myelogenous leukemia, acute myeloid leukemia or acute lymphoblastic leukemia. The fusion gene can be BCR-ABL, AML-ETO, CBFB-MYH11, E2A-PBX1, MLL-AF4, PML-RARA, or TEL-AML1.

In certain embodiments, each of said label monomers can be a fluorochrome moiety, a fluorescent moiety, a dye moiety or a chemiluminescent moiety. The unique label for each target-specific probe can be composed of 4 or 5 label monomers.

The disclosure also provides a method for diagnosing leukemia, a specific subtype of leukemia or determining a genetic aberration underlying leukemia in a subject. In one embodiment, the method includes providing a sample from the subject and contacting the sample with one or more target-specific probes. Each of the one or more target-specific probes includes a target-specific region that binds to one target nucleic acid analyte; and a region to which is attached a plurality of label monomers that create a unique label for each target-specific probe. The label has a detectable signal that distinguishes one target-specific probe which binds to a first target nucleic acid from another target-specific probe that binds to a different second target nucleic acid. One or more targets of the one or more target-specific probes include a fusion gene or mRNA transcribed from said fusion gene. The fusion gene is the result of the fusion of two or more genes in a patient at the onset of or during progression of leukemia. When the fusion gene is detected the subject is diagnosed with leukemia, a specific subtype of leukemia or the genetic aberration underlying leukemia in a subject is determined.

The fusion gene can be BCR-ABL, AML-ETO, CBFB-MYH11, E2A-PBX1, MLL-AF4, PML-RARA, or TEL-AML1. The leukemia can be chronic myelogenous leukemia, acute myeloid leukemia or acute lymphoblastic leukemia.

In certain embodiments, at least one of the one or more target-specific probes can have a target that is the sequence of the junction of the two genes that are fused. The one or more target-specific probes can include a target-specific region with one or more mismatches to the target of the target-specific region.

In other embodiments, each of the label monomers can be a fluorochrome moiety, a fluorescent moiety, a dye moiety or a chemiluminescent moiety. The unique label for each target-specific probe can be composed of 4 or 5 label monomers.

The disclosure also provides a method for diagnosing leukemia, a specific subtype of leukemia or determining a genetic aberration underlying leukemia in a subject. In one embodiment, the method includes providing a sample from the subject and contacting the sample with a probe pair. The probe pair includes a first probe and a second probe. The first probe is made up, at least in part, of a complex including a first molecule with a first label attachment region to which are attached one or more label monomers that emit light constituting a first signal. The first probe also includes a second label attachment region, which is non-overlapping with the first label attachment region, to which are attached one or more label monomers that emit light constituting a second signal. The first probe also includes a first target-specific sequence attached to the first molecule. The second probe is made up, at least in part, of a second molecule, comprising a second target-specific sequence and an affinity tag. The first target-specific sequence and the second target-specific sequence bind to different regions of the same target molecule. The target molecule is a fusion gene or mRNA transcribed from said fusion gene. The fusion gene is the result of the fusion of two or more genes in a patient at the onset of or during progression of leukemia. When said probe pair is bound to its target molecule, the identity of the first and second signals and their locations relative to each other constitute at least part of a code that identifies the target molecule. Also, when the fusion gene is detected the subject is diagnosed with leukemia, a specific subtype of leukemia or the genetic aberration underlying leukemia is determined.

In certain embodiments, the fusion gene can include the fusion of at least a portion of a first gene and at least a portion of a second gene. The first target-specific sequence can hybridize to a portion of the first gene and the second target-specific sequence hybridizes to a portion of the second gene. The first target-specific sequence can also hybridize to a sequence adjacent to a sequence that the second target-specific sequence hybridizes to on the fusion gene.

In other embodiments, the first target-specific sequence can hybridize to a portion of the first gene and a portion of the second gene. The first target-specific sequence can also hybridize to a sequence adjacent to a sequence that the second target-specific sequence hybridizes to on the fusion gene. At least one of the target-specific sequences can include a region with one or more mismatches to the target of the target-specific sequence.

In other embodiments, the second target-specific sequence can hybridize to a portion of the first gene and a portion of the second gene. The first target-specific sequence can also hybridize to a sequence adjacent to a sequence that the second target-specific sequence hybridizes to on the fusion gene. At least one of the target-specific sequences can include a region with one or more mismatches to the target of the target-specific sequence.

The leukemia can be chronic myelogenous leukemia, acute myeloid leukemia or acute lymphoblastic leukemia. The fusion gene can be BCR-ABL, AML-ETO, CBFB-MYH11, E2A-PBX1, MLL-AF4, PML-RARA, or TEL-AML1.

Each of said label monomers can be a fluorochrome moiety, a fluorescent moiety, a dye moiety or a chemiluminescent moiety. The unique label for each target-specific probe can be composed of 4 or 5 label monomers.

The disclosure also provides a kit. In one embodiment, the kit includes one or more reporter probes and one or more capture probes. The reporter probe and the capture probe each bind specifically to a fusion gene. The fusion gene is the result of the fusion of two or more genes in a patient at the onset of or during progression of leukemia.

The fusion gene can be BCR-ABL, AML-ETO, CBFB-MYH11, E2A-PBX1, MLL-AF4, PML-RARA, or TEL-AML1. The kit can include one or more reporter probes and one or more capture probes from Table 2.

BRIEF DESCRIPTION OF THE DRAWINGS

FIG. 2E is a bar graph showing the relative expression of various gene fusions in the KCL-22 cell line.

FIG. 2F is a bar graph showing the relative expression of various gene fusions in the MV4-11 cell line.

DETAILED DESCRIPTION OF THE INVENTION

Figure 1A:
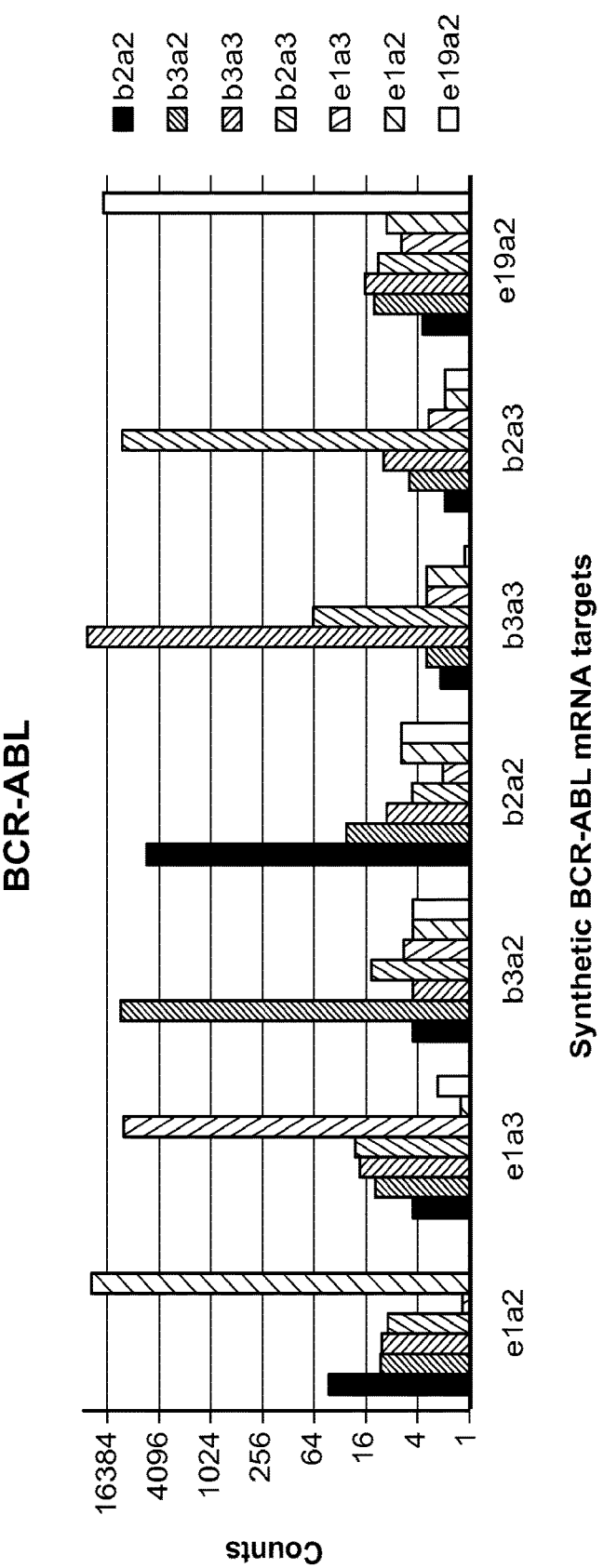
FIG. 1A is a bar graph showing counts for probes for the BCR-ABL gene fusion when exposed to gene fragments of the BCR-ABL gene fusion and non-specific targets.

This disclosure describes compositions and methods for the diagnosis of leukemia, diagnosis of the subtype of leukemia present in a subject and determination of the genetic aberration underlying leukemia in a subject. The onset and progression of leukemia is associated with the formation of several fusion genes. These fusion genes include BCR-ABL, AML-ETO, CBFB-MYH11, E2A-PBX1, MLL-AF4, PML-RARA, or TEL-AML1. The compositions disclosed herein are nucleic acid probes used to detect the presence of these fusion genes.

The detection of these fusion genes can be used to detect the presence of leukemia and also what type of leukemia is present. For example, a BCR-ABL fusion gene is associated with chronic myelogenous leukemia. AML-ETO, CBFB-MYH11, MLL-AF4, and PML-RARA fusion genes are associated with acute myeloid leukemia. E2A-PBX1 and TEL-AML1 fusion genes are associated with acute lymphoblastic leukemia. In addition, specific isoforms of a given fusion may indicate a specific sub-type of disease.

The presence of certain gene fusions in certain types of leukemia is associated with differing prognoses in the outcome of the disease for a subject. Thus, the detection of various gene fusions can be used to provide a prognosis for a subject with leukemia.

Preferably, the nucleic acid probes used according to the methods of the disclosure are nanoreporters. A fully assembled and labeled nanoreporter comprises two main portions, a target-specific sequence that is capable of binding to a target molecule, and a labeled region which emits a "code" of signals (the "nanoreporter code") associated with the target-specific sequence.

Upon binding of the nanoreporter to the target molecule, the nanoreporter code identifies the target molecule to which the nanoreporter is bound.

Nanoreporters

Many nanoreporters, referred to as singular nanoreporters, are composed of one molecular entity. However, to increase the specificity of a nanoreporter and/or to improve the kinetics of its binding to a target molecule, a preferred nanoreporter is a dual nanoreporter composed of two molecular entities, each containing a different target-specific sequence that binds to a different region of the same target molecule. In a dual nanoreporter, at least one of the two nanoreporter probes is labeled. This labeled nanoreporter probe is referred to herein as a "reporter probe". The other nanoreporter probe is not necessarily labeled. Such unlabeled components of dual nanoreporters are referred to herein as "capture probes" and often have affinity tags attached, such as biotin, which are useful to immobilize and/or stretch the complex containing the dual nanoreporter and the target molecule to allow visualization and/or imaging of the complex. When both probes are labeled or both have affinity tags, the probe with more label monomer attachment regions is referred to as the reporter probe and the other probe in the pair is referred to as a capture probe.

For both single and dual nanoreporters, a fully assembled and labeled nanoreporter probe comprises two main portions, a target-specific sequence that is capable of binding to a target molecule, and a labeled portion which provides a "code" of signals associated with the target-specific sequence. Upon binding of the nanoreporter probe to the target molecule, the code identifies the target molecule to which the nanoreporter is bound.

Nanoreporters are modular structures. In some embodiments, the nanoreporter comprises a plurality of different detectable molecules. In some embodiments, a labeled nanoreporter, is a molecular entity containing certain basic elements: (i) a plurality of unique label attachment regions attached in a particular, unique linear combination, and (ii) complementary polynucleotide sequences attached to the label attachment regions of the backbone. In some embodiments, the labeled nanoreporter comprises 2, 3, 4, 5, 6, 7, 8, 9, 10 or more unique label attachment regions attached in a particular, unique linear combination, and complementary polynucleotide sequences attached to the label attachment regions of the backbone. In some embodiments, the labeled nanoreporter comprises 6 or more unique label attachment regions attached in a particular, unique linear combination, and complementary polynucleotide sequences attached to the label attachment regions of the backbone. A nanoreporter probe further comprises a target-specific sequence, also attached to the backbone.

The term label attachment region includes a region of defined polynucleotide sequence within a given backbone that may serve as an individual attachment point for a detectable molecule. In some embodiments, the label attachment regions comprise designed sequences.

In some embodiments, the label nanoreporter also comprises a backbone containing a constant region. The term constant region includes tandemly-repeated sequences of about 10 to about 25 nucleotides that are covalently attached to a nanoreporter. The constant region can be attached at either the 5' region or the 3' region of a nanoreporter, and may be utilized for capture and immobilization of a nanoreporter for imaging or detection, such as by attaching to a solid substrate a sequence that is complementary to the constant region. In certain aspects, the constant region contains 2, 3, 4, 5, 6, 7, 8, 9, 10, or more tandemly-repeated sequences, wherein the repeat sequences each comprise about 8, 9, 10, 11, 12, 13, 14, 15, 16, 17, 18, 19, 20, 21, 22, 23, 24, 25, 26, 27, 28, 29, 30, or more nucleotides, including about 12-18, 13-17, or about 14-16 nucleotides.

The nanoreporters described herein can comprise synthetic, designed sequences. In some embodiments, the sequences contain a fairly regularly-spaced pattern of a nucleotide (e.g. adenine) residue in the backbone. In some embodiments, a nucleotide is spaced at least an average of 8, 9, 10, 12, 15, 16, 20, 30, or 50 bases apart. In some embodiments, a nucleotide is spaced at least an average of 8 to 16 bases apart. In some embodiments, a nucleotide is spaced at least an average of 8 bases apart. This allows for a regularly spaced complementary nucleotide in the complementary polynucleotide sequence having attached thereto a detectable molecule. For example, in some embodiments, when the nanoreporter sequences contain a fairly regularly-spaced pattern of adenine residues in the backbone, whose complement is a regularly-spaced pattern of uridine (U) residues in complementary RNA segments, the in vitro transcription of the segments can be done using an aminoallyl-modified uridine base, which allows the covalent amine coupling of dye molecules at regular intervals along the segment. In some embodiments, the sequences contain about the same number or percentage of a nucleotide (e.g. adenine) that is spaced at least an average of 8, 9, 10, 12, 15, 16, 20, 30, or 50 bases apart in the sequences. This allows for similar number or percentages in the complementary polynucleotide sequence having attached thereto a detectable molecule. Thus, in some embodiments, the sequences contain a nucleotide that is not regularly-spaced but that is spaced at least an average of 8, 9, 10, 12, 15, 16, 20, 30, or 50 bases apart. In some embodiments, 20%, 30%, 50%, 60%, 70%, 80%, 90% or 100% of the complementary nucleotide is coupled to a detectable molecule. For instance, in some embodiments, when the nanoreporter sequences contain a similar percentage of adenine residues in the backbone and the in vitro transcription of the complementary segments is done using an aminoallyl-modified uridine base, 20%, 30%, 50%, 60%, 70%, 80%, 90% or 100% of the aminoallyl-modified uridine base can be coupled to a detectable molecule. Alternatively, the ratio of aminoallyl-modified uridine bases and uridine bases can be changed during the in vitro transcription process to achieve the desired number of sites which can be attached to a detectable molecule. For example, in vitro transcription process can take place in the presence of a mixture with a ratio of 1/1 of uridine to aminoallyl-modified uridine bases, when some or all the aminoallyl-modified uridine bases can be coupled to a detectable molecule.

In some embodiments, the nanoreporters described herein have a fairly consistent melting temperature (Tm). Without intending to be limited to any theory, the Tm of the nanoreporters described herein provides for strong bonds between the nanoreporter backbone and the complementary polynucleotide sequence having attached thereto a detectable molecule, therefore, preventing dissociation during synthesis and hybridization procedures. In addition, the consistent Tm among a population of nanoreporters allows for the synthesis and hybridization procedures to be tightly optimized, as the optimal conditions are the same for all spots and positions. In some embodiments, the sequences of the nanoreporters have a 50% guanine/cytosine (G/C), with no more than three G's in a row. Thus, in some embodiments, the disclosure provides a population of nanoreporters in which the Tm among the nanoreporters in the population is fairly consistent. In some embodiments, the disclosure provides a population of nanoreporters in which the Tm of the complementary polynucleotide sequences when hybridized to its label attachment regions is about 80° C., 85° C., 90° C., 100° C. or higher. In some embodiments, the disclosure provides a population of nanoreporters in which the Tm of the complementary polynucleotide sequences when hybridized to its label attachment regions is about 80° C. or higher.

In some embodiments, the nanoreporters described herein have minimal or no secondary structures, such as any stable intra-molecular base-paring interaction (e.g. hairpins). Without intending to be limited to any theory, the minimal secondary structure in the nanoreporters provides for better hybridization between the nanoreporter backbone and the polynucleotide sequence having attached thereto a detectable molecule. In addition, the minimal secondary structure in the nanoreporters provides for better detection of the detectable molecules in the nanoreporters. In some embodiments, the nanoreporters described herein have no significant intra-molecular pairing under annealing conditions of 75° C., 1×SSPE. Secondary structures can be predicted by programs known in the art such as MFOLD. In some embodiments, the nanoreporters described herein contain less than 1% of inverted repeats in each strand, wherein the inverted repeats are 9 bases or greater. In some embodiments, the nanoreporters described herein contain no inverted repeats in each strand. In some embodiments, the nanoreporters do not contain any inverted repeat of 9 nucleotides or greater across a sequence that is 1100 base pairs in length. In some embodiments, the nanoreporters do not contain any inverted repeat of 7 nucleotides or greater across any 100 base pair region. In some embodiments, the nanoreporters described herein contain less than 1% of inverted repeats in each strand, wherein the inverted repeats are 9 nucleotides or greater across a sequence that 1100 base pairs in length. In some embodiments, the nanoreporters described herein contain less than 1% of inverted repeats in each strand, wherein the inverted repeats are 7 nucleotides or greater across any 100 base pair region. In some embodiments, the nanoreporters described herein contain a skewed strand specific content such that one strand is CT-rich and the other is GA-rich.

The disclosure also provides unique nanoreporters. In some embodiments, the nanoreporters described herein contain less that 1% of direct repeats. In some embodiments, the nanoreporters described herein contain no direct repeats. In some embodiments, the nanoreporters do not contain any direct repeat of 9 nucleotides or greater across a sequence that 1100 base pairs in length. In some embodiments, the labeled nanoreporters do not contain any direct repeat of 7 nucleotides or greater across any 100 base pair region. In some embodiments, the nanoreporters described herein contain less than 1% of direct repeats in each strand, wherein the direct repeats are 9 nucleotides or greater across a sequence that 1100 base pairs in length. In some embodiments, the nanoreporters described herein contain less than 1% of direct repeats in each strand, wherein the direct repeats are 7 nucleotides or greater across any 100 base pair region. In some embodiments, the nanoreporters described herein contain less than 85, 80, 70, 60, 50, 40, 30, 20, 10, or 5% homology to any other sequence used in the backbones or to any sequence described in the REFSEQ public database. In some embodiments, the nanoreporters described herein contain less than 85% homology to any other sequence used in the backbones or to any sequence described in the REFSEQ public database. In some embodiments, the nanoreporters described herein contain less than 20, 16, 15, 10, 9, 7, 5, 3, 2 contiguous bases of homology to any other sequence used in the backbones or to any sequence described in the REFSEQ public database. In some embodiments, the nanoreporters described herein have no more than 15 contiguous bases of homology and no more than 85% identity across the entire length of the nanoreporter to any other sequence used in the backbones or to any sequence described in the REFSEQ public database.

In some embodiments, the sequence characteristics of the nanoreporter probes described herein provide sensitive detection of a target molecule. For instance, the binding of the nanoreporter probes to target molecules which results in the identification of the target molecules can be performed by individually detecting the presence of the nanoreporter.

This can be performed by individually counting the presence of one or more of the nanoreporter molecules in a sample.

The complementary polynucleotide sequences attached to a nanoreporter backbone serve to attach detectable molecules, or label monomers, to the nanoreporter backbone. The complementary polynucleotide sequences may be directly labeled, for example, by covalent incorporation of one or more detectable molecules into the complementary polynucleotide sequence. Alternatively, the complementary polynucleotide sequences may be indirectly labeled, such as by incorporation of biotin or other molecule capable of a specific ligand interaction into the complementary polynucleotide sequence. In such instances, the ligand (e.g., streptavidin in the case of biotin incorporation into the complementary polynucleotide sequence) may be covalently attached to the detectable molecule. Where the detectable molecules attached to a label attachment region are not directly incorporated into the complementary polynucleotide sequence, this sequence serves as a bridge between the detectable molecule and the label attachment region, and may be referred to as a bridging molecule, e.g., a bridging nucleic acid.

The nucleic-acid based nanoreporter and nanoreporter-target complexes described herein comprise nucleic acids, which may be affinity-purified or immobilized using a nucleic acid, such as an oligonucleotide, that is complementary to the constant region or the nanoreporter or target nucleic acid. As noted above, in some embodiments the nanoreporters comprise at least one constant region, which may serve as an affinity tag for purification and/or for immobilization (for example to a solid surface). The constant region typically comprises two or more tandemly-repeated regions of repeat nucleotides, such as a series of 15-base repeats. In such exemplary embodiments, the nanoreporter, whether complexed to a target molecule or otherwise, can be purified or immobilized by an affinity reagent coated with a 15-base oligonucleotide which is the reverse complement of the repeat unit.

Nanoreporters, or nanoreporter-target molecule complexes, can be purified in two or more affinity selection steps. For example, in a dual nanoreporter, one probe can comprise a first affinity tag and the other probe can comprise a second (different) affinity tag. The probes are mixed with target molecules, and complexes comprising the two probes of the dual nanoreporter are separated from unbound materials (e.g., the target or the individual probes of the nanoreporter) by affinity purification against one or both individual affinity tags. In the first step, the mixture can be bound to an affinity reagent for the first affinity tag, so that only probes comprising the first affinity tag and the desired complexes are purified. The bound materials are released from the first affinity reagent and optionally bound to an affinity reagent for the second affinity tag, allowing the separation of complexes from probes comprising the first affinity tag. At this point only full complexes would be bound. The complexes are finally released from the affinity reagent for the second affinity tag and then preferably stretched and imaged. The affinity reagent can be any solid surface coated with a binding partner for the affinity tag, such as a column, bead (e.g., latex or magnetic bead) or slide coated with the binding partner. Immobilizing and stretching nanoreporters using affinity reagents is fully described in U.S. Publication No. 2010/0161026, which is incorporated by reference herein in its entirety.

The sequence of signals provided by the label monomers associated with the various label attachment regions of the backbone of a given nanoreporter allows for the unique identification of the nanoreporter. For example, when using fluorescent labels, a nanoreporter having a unique identity or unique spectral signature is associated with a target-specific sequence that recognizes a specific target molecule or a portion thereof. When a nanoreporter is exposed to a mixture containing the target molecule under conditions that permit binding of the target-specific sequence(s) of the nanoreporter to the target molecule, the target-specific sequence(s) preferentially bind(s) to the target molecule. Detection of the nanoreporter signal, such as the spectral code of a fluorescently labeled nanoreporter, associated with the nanoreporter allows detection of the presence of the target molecule in the mixture (qualitative analysis). Counting all the label monomers associated with a given spectral code or signature allows the counting of all the molecules in the mixture associated with the target-specific sequence coupled to the nanoreporter (quantitative analysis). Nanoreporters are thus useful for the diagnosis or prognosis of different biological states (e.g., disease vs. healthy) by quantitative analysis of known biological markers. Moreover, the exquisite sensitivity of single molecule detection and quantification provided by the nanoreporters described herein allows for the identification of new diagnostic and prognostic markers, including those whose fluctuations among the different biological states is too slight detect a correlation with a particular biological state using traditional molecular methods. The sensitivity of nanoreporter-based molecular detection permits detailed pharmacokinetic analysis of therapeutic and diagnostic agents in small biological samples.

Many nanoreporters, referred to as singular nanoreporters, are composed of one molecular entity. However, to increase the specificity of a nanoreporter and/or to improve the kinetics of its binding to a target molecule, a nanoreporter can be a dual nanoreporter composed of two molecular entities, each containing a different target-specific sequence that binds to a different region of the same target molecule. In a dual nanoreporter, at least one of the two molecular entities is labeled. The other molecular entity need not necessarily be labeled. Such unlabeled components of dual nanoreporters may be used as capture probes and optionally have affinity tags attached, such as biotin, which are useful to immobilize and/or stretch the complex containing the dual nanoreporter and the target molecule to allow visualization and/or imaging of the complex. For instance, in some embodiments, a dual nanoreporter with a 6-position nanoreporter code uses one 6-position coded nanoreporter (also referred to herein as a reporter probe) and a capture probe. In some embodiments, a dual nanoreporter with a 6-position nanoreporter code can be used, using one capture probe with an affinity tag and one 6-position nanoreporter component. In some embodiments an affinity tag is optionally included and can be used to purify the nanoreporter or to immobilize the nanoreporter (or nanoreporter-target molecule complex) for the purpose of imaging.

In some embodiments, the nucleotide sequences of the individual label attachment regions within each nanoreporter are different from the nucleotide sequences of the other label attachment regions within that nanoreporter, preventing rearrangements, such recombination, sharing or swapping of the label polynucleotide sequences. The number of label attachment regions to be formed on a backbone is based on the length and nature of the backbone, the means of labeling the nanoreporter, as well as the type of label monomers providing a signal to be attached to the label attachment regions of the backbone. In some embodiments, the complementary nucleotide sequence of each label attachment region is assigned a specific detectable molecule.

The disclosure also provides labeled nanoreporters wherein one or more label attachment regions are attached to a corresponding detectable molecule, each detectable molecule providing a signal. For example, in some embodiments, a labeled nanoreporter according to the disclosure is obtained when at least three detectable molecules are attached to three corresponding label attachment regions of the backbone such that these labeled label attachment regions, or spots, are distinguishable based on their unique linear arrangement. A "spot," in the context of nanoreporter detection, is the aggregate signal detected from the label monomers attached to a single label attachment site on a nanoreporter, and which, depending on the size of the label attachment region and the nature (e.g., primary emission wavelength) of the label monomer, may appear as a single point source of light when visualized under a microscope. Spots from a nanoreporter may be overlapping or non-overlapping. The nanoreporter code that identifies that target molecule can comprise any permutation of the length of a spot, its position relative to other spots, and/or the nature (e.g., primary emission wavelength(s)) of its signal. Generally, for each probe or probe pair described herein, adjacent label attachment regions are non-overlapping, and/or the spots from adjacent label attachment regions are spatially and/or spectrally distinguishable, at least under the detection conditions (e.g., when the nanoreporter is immobilized, stretched and observed under a microscope, as described in U.S. Publication No. 2010/0112710, incorporated herein by reference).

Occasionally, reference is made to a spot size as a certain number of bases or nucleotides. As would be readily understood by one of skill in the art, this refers to the number of bases or nucleotides in the corresponding label attachment region.

The order and nature (e.g., primary emission wavelength(s), optionally also length) of spots from a nanoreporter serve as a nanoreporter code that identifies the target molecule capable of being bound by the nanoreporter through the nanoreporter's target specific sequence(s). When the nanoreporter is bound to a target molecule, the nanoreporter code also identifies the target molecule. Optionally, the length of a spot can be a component of the nanoreporter code.

Detectable molecules providing a signal associated with different label attachment regions of the backbone can provide signals that are indistinguishable under the detections conditions ("like" signals), or can provide signals that are distinguishable, at least under the detection conditions (e.g., when the nanoreporter is immobilized, stretched and observed under a microscope).

The disclosure also provides a nanoreporter wherein two or more detectable molecules are attached to a label attachment region. The signal provided by the detectable molecules associated with said label attachment region produces an aggregate signal that is detected. The aggregate signal produced may be made up of like signals or made up of at least two distinguishable signals (e.g., spectrally distinguishable signals).

In one embodiment, a nanoreporter includes at least three detectable molecules providing like signals attached to three corresponding label attachment regions of the backbone and said three detectable molecules are spatially distinguishable. In another embodiment, a nanoreporter includes at least three detectable molecules providing three distinguishable signals attached to three neighboring label attachment regions, for example three adjacent label attachment regions, whereby said at least three label monomers are spectrally distinguishable.

In other embodiments, a nanoreporter includes spots providing like or unlike signals separated by a spacer region, whereby interposing the spacer region allows the generation of dark spots, which expand the possible combination of uniquely detectable signals. The term "dark spot" refers to a lack of signal from a label attachment site on a nanoreporter. Dark spots can be incorporated into the nanoreporter code to add more coding permutations and generate greater nanoreporter diversity in a nanoreporter population. In one embodiment, the spacer regions have a length determined by the resolution of an instrument employed in detecting the nanoreporter.

In other embodiments, a nanoreporter includes one or more "double spots." Each double spot contains two or more (e.g., three, four or five) adjacent spots that provide like signals without being separated by a spacer region. Double spots can be identified by their sizes.

A detectable molecule providing a signal described herein may be attached covalently or non-covalently (e.g., via hybridization) to a complementary polynucleotide sequence that is attached to the label attachment region. The label monomers may also be attached indirectly to the complementary polynucleotide sequence, such as by being covalently attached to a ligand molecule (e.g., streptavidin) that is attached through its interaction with a molecule incorporated into the complementary polynucleotide sequence (e.g., biotin incorporated into the complementary polynucleotide sequence), which is in turn attached via hybridization to the backbone.

A nanoreporter can also be associated with a uniquely detectable signal, such as a spectral code, determined by the sequence of signals provided by the label monomers attached (e.g., indirectly) to label attachment regions on the backbone of the nanoreporter, whereby detection of the signal allows identification of the nanoreporter.

In other embodiments, a nanoreporter also includes an affinity tag attached to the reporter probe backbone, such that attachment of the affinity tag to a support allows backbone stretching and resolution of signals provided by label monomers corresponding to different label attachment regions on the backbone. Nanoreporter stretching may involve any stretching means known in the art including but not limited to, means involving physical, hydrodynamic or electrical means. The affinity tag may comprise a constant region.

In other embodiments, a nanoreporter also includes a target-specific sequence coupled to the backbone. The target-specific sequence is selected to allow the nanoreporter to recognize, bind or attach to a target molecule. The nanoreporters described herein are suitable for identification of target molecules of all types. For example, appropriate target-specific sequences can be coupled to the backbone of the nanoreporter to allow detection of a target molecule. Preferably the target molecule is DNA (including cDNA), RNA (including mRNA and cRNA), a peptide, a polypeptide, or a protein.

One embodiment of the disclosure provides increased flexibility in target molecule detection with label monomers described herein. In this embodiment, a dual nanoreporter comprising two different molecular entities, each with a separate target-specific region, at least one of which is labeled, bind to the same target molecule. Thus, the target-specific sequences of the two components of the dual nanoreporter bind to different portions of a selected target molecule, whereby detection of the spectral code associated with the dual nanoreporter provides detection of the selected target molecule in a biomolecular sample contacted with said dual nanoreporter.

The disclosure also provides a method of detecting the presence of a specific target molecule in a biomolecular sample comprising: (i) contacting said sample with a nanoreporter as described herein (e.g., a singular or dual nanoreporter) under conditions that allow binding of the target-specific sequences in the dual nanoreporter to the target molecule and (ii) detecting the spectral code associated with the dual nanoreporter. Depending on the nanoreporter architecture, the dual nanoreporter may be labeled before or after binding to the target molecule.

The uniqueness of each nanoreporter probe in a population of probe allows for the multiplexed analysis of a plurality of target molecules. For example, in some embodiments, each nanoreporter probe contains six label attachment regions, where each label attachment region of each backbone is different from the other label attachment regions in that same backbone. If the label attachment regions are going to be labeled with one of four colors and there are 24 possible unique sequences for the label attachment regions and each label attachment region is assigned a specific color, each label attachment region in each backbone will consist of one of four sequences. There will be 4096 possible nanoreporters in this example. The number of possible nanoreporters can be increased, for example, by increasing the number of colors, increasing the number of unique sequences for the label attachment regions and/or increasing the number of label attachment regions per backbone. Likewise the number of possible nanoreporters can be decreased by decreasing the number of colors, decreasing the number of unique sequences for the label attachment regions and/or decreasing the number of label attachment regions per backbone.

In certain embodiments, the methods of detection are performed in multiplex assays, whereby a plurality of target molecules are detected in the same assay (a single reaction mixture). In a preferred embodiment, the assay is a hybridization assay in which the plurality of target molecules are detected simultaneously. In certain embodiments, the plurality of target molecules detected in the same assay is, at least 2, at least 5 different target molecules, at least 10 different target molecules, at least 20 different target molecules, at least 50 different target molecules, at least 75 different target molecules, at least 100 different target molecules, at least 200 different target molecules, at least 500 different target molecules, or at least 750 different target molecules, or at least 1000 different target molecules. In other embodiments, the plurality of target molecules detected in the same assay is up to 50 different target molecules, up to 100 different target molecules, up to 150 different target molecules, up to 200 different target molecules, up to 300 different target molecules, up to 500 different target molecules, up to 750 different target molecules, up to 1000 different target molecules, up to 2000 different target molecules, or up to 5000 different target molecules. In yet other embodiments, the plurality of target molecules detected is any range in between the foregoing numbers of different target molecules, such as, but not limited to, from 20 to 50 different target molecules, from 50 to 200 different target molecules, from 100 to 1000 different target molecules, from 500 to 5000 different target molecules, and so on and so forth.

In certain embodiments, nanoreporters for detecting the presence of fusion genes contain both a reporter probe and a capture probe that hybridize to the fusion gene at different positions. In one embodiment, the target-specific regions of the capture and reporter probe hybridize to sequences on either side of the border of the fusion between the two fused genes. Optionally, the target-specific regions hybridize to regions adjacent to each other on either side of the border of fusion. The sequences to which the target-specific regions of the reporter and capture probes hybridize can also be 1, 2, 3, 4, 5, 6, 7, 8, 9, 10, 11, 12, 13, 14, 15, 16, 17, 18, 19, 20 or more base pairs apart.

In another embodiment, the reporter probe's target-specific region hybridizes to a sequence that spans the fusion junction while the target-specific region of the capture probe hybridizes to a sequence upstream or downstream of the reporter probe's target. In another embodiment, the capture probe's target-specific region hybridizes to a sequence that spans the fusion junction while the target-specific region of the reporter probe hybridizes to a sequence upstream or downstream of the reporter probe's target. Optionally, the target sequences of the reporter and capture probes are adjacent. The sequences to which the target-specific regions of the reporter and capture probes hybridize can also be 1, 2, 3, 4, 5, 6, 7, 8, 9, 10, 11, 12, 13, 14, 15, 16, 17, 18, 19, 20 or more base pairs apart. In certain embodiments, the target-specific region of a probe has 1, 2, 3, 4, 5 or more mismatches introduced into the target-specific sequence. The sequences which come together to form the junction of a fusion gene can be GC rich, resulting in a high melting temperature for the probe on both sides of the junction. Thus, in certain situations, the probe has an increased propensity to cross-hybridize with isoforms containing the same sequence as only one side of the junction, rather than requiring the presence of both sequences for successful hybridization. Introduction of certain mismatches into the probe produces a decreased melting temperature and higher specificity. In preferred embodiments, probes that hybridize to a sequence that encompasses the junction of the fusion genes have 1, 2, 3, 4, 5, or more mismatches. Additional disclosure regarding nanoreporters can be found in International Publication Nos. WO 07/076,129 and WO 07/076,132, the contents of which are incorporated herein in their entireties. Further, the term nucleic acid probes and nanoreporters can include the rationally designed (e.g. synthetic sequences) described in International Publication No. WO 2010/019826, incorporated herein by reference in its entirety.

Examples of various probes and their targets are provided below in Table 1.

TABLE 1

| Gene Fusion | Isoform | | SEQ ID NO: |
|---|---|---|---|
| | | Reporter Probe | |
| BCR-ABL | b2a2 | TGGCCGCTGAAGGGCTT CTTCCTTATTGATGGTCA | 1 |
| BCR-ABL | b3a2 | TGGCCGCTGAAGGGCTT TTGAACTCTGCTTAAATC | 2 |
| BCR-ABL | e1a2 | TGGCCGCTGAAGGGCTT CTGCATCTCCATGGAAGG(*) | 3 |

TABLE 1-continued

| Gene Fusion | Isoform | | SEQ ID NO: |
|---|---|---|---|
| BCR-ABL | e19a2 | TGGCCGCTGAAGGGCTT TGACGTCGAAAGCTGCCT(*) | 4 |
| BCR-ABL | b3a3 | GACCCGGAGCTTTTCAC TTGAACTCTGCTTAAATC | 5 |
| BCR-ABL | b2a3 | GACCCGGAGCTTTTCAC CTTCCTTATTGATGGTCA | 6 |
| BCR-ABL | e1a3 | GACCCGGAGCTTTTCAC CTGCATCTCCATGGAAGG(*) | 7 |
| AML-ETO | | CTTCACATCCACAGGTGAGTCTGGCATTGTGGAGTGCTTCTCAGTACGAT(+) | 8 |
| CBFb-MYH11 | e5e12 | TCCAGGGCCCGCTTGGACTTCTCCAGCTCATGGAC(+) | 9 |
| CBFb-MYH11 | e5e8 | CGGCCTCGTTAAGCATCCCTGTGACGCTCTCAACTTCATT(+) | 10 |
| CBFb-MYH11 | e5e7 | AGCGTCTGCTTATTCTTGTCTAGGTTCGCCTTGGC(+) | 11 |
| E2A-PBX1 | e13-insertion-n27-e2 | AAAAGGTTCCAGGTGACCGAACACTTTCAT CACTG | 12 |
| E2A-PBX1 | e13e2 | TCCTCGGATACTCAAAA CACTGTAGGAGTCGGGAG | 13 |
| MLL-AF4 | e8e7 | AGATGTATCATATTGTT CTGATTCTGGTGGTGGAG | 14 |
| MLL-AF4 | e9e5 | CATGAATGGGTCATTTC CTTTTCTTTTGGTTTTTG | 15 |
| MLL-AF4 | e9e4 | TCATTGGAGTAGGTCTG CTTTTCTTTTGGTTTTTG | 16 |
| MLL-AF4 | e10e5 | CATGAATGGGTCATTTC CTTAAAGTCCACTCTGAT | 17 |
| MLL-AF4 | e10e4 | TCATTGGAGTAGGTCTG CTTAAAGTCCACTCTGAT | 18 |
| MLL-AF4 | e11e5 | CATGAATGGGTCATTTC CTATACATGCCCACTACT(*) | 19 |
| MLL-AF4 | e11e4 | TCATTGGAGTAGGTCTG CTATACATGCCCACTACT(*) | 20 |
| PML-RARA | bcr1 (e6e3) | TCTGGGTCTCAATGG CTGACTCCCAAGCGCCACTG(*) | 21 |
| PML-RARA | bcr3 (e3e3) | TCTGGGTCTCAATGG CTTTCCACTGGGTGATGCAA(*) | 22 |
| PML-RARA | bcr2 (e6partial_e3) | GCTCTGGGTCTCAATGG TTCCTATGACGGGACTCC(*) | 23 |
| TEL-AML1 | e5e2 | TCCCCTAGGGCCACCAC CTGCTATTCTCACAATGG(*) | 24 |
| TEL-AML1 | e5e3 | CAGAGTGAAGCTTTTCC CTGCTATTCTACCAATGG(*) | 25 |
| Capture Probe | | | |
| BCR-ABL | b2a2 | GCGGAATGCTGTGGACAGTCTGGAGTTTCACACACGAGTT | 26 |
| BCR-ABL | b3a2 | CAGTGGCTGAGTGGACGATGACATTCAGAAACCCATAGAGCCCCGGAGAC | 27 |
| BCR-ABL | e1a2 | CGCCCTCGCCATCGTTGGGCCAGATCTGCCCGGTCTTGCG | 28 |
| BCR-ABL | e19a2 | TCAGTGCCTGGATGTCCGTGGCCACACCGGACACG | 29 |
| BCR-ABL | b3a3 | CAGTGGCTGAGTGGACGATGACATTCAGAAACCCA | 30 |
| BCR-ABL | b2a3 | GCGGAATGCTGTGGACAGTCTGGAGTTTCACACAC | 31 |
| BCR-ABL | e1a3 | CGCCCTCGCCATCGTTGGGCCAGATCTGCCCGGTCTTGCG | 32 |
| AML-ETO | | TTCGAGGTTCTCGGGGCCCATCCACTGTGATTTTGATGGCTCTGTGGTAG | 33 |
| CBFb-MYH11 | e5e12 | CAGTTACTGCCAGCAGCTGTGAAACTCTCACCTCCATTTC | 34 |

TABLE 1-continued

| Gene Fusion | Isoform | | SEQ ID NO: |
|---|---|---|---|
| CBFb-MYH11 | e5e8 | CAGTTACTGCCAGCAGCTGTGAAACTCTCACCTCCATTTC | 35 |
| CBFb-MYH11 | e5e7 | CAGTTACTGCCAGCAGCTGTGAAACTCTCACCTCCATTTC | 36 |
| E2A-PBX1 | e13-insertion-n27-e2 | TAGGAGTCGGGAGGCCGAGACAGGTCAGGGAGGGT | 37 |
| E2A-PBX1 | e13e2 | GCCGAGACAGGTCAGGGAGGGTGCCTGGCTGGCTG | 38 |
| MLL-AF4 | e8e7 | GCTGCTTTTTCTTGGGCTCACTAGGAGTGGTTTTG | 39 |
| MLL-AF4 | e9e5 | TTTTACAGGGATACTTGGGCGGGGAGCCACTTTTT | 40 |
| MLL-AF4 | e9e4 | TTTTACAGGGATACTTGGGCGGGGAGCCACTTTTT | 41 |
| MLL-AF4 | e10e5 | CCTGTGGACTCCATCTGCTGGAATTTTTTGCTTAG | 42 |
| MLL-AF4 | e10e4 | CCTGTGGACTCCATCTGCTGGAATTTTTTGCTTAG | 43 |
| MLL-AF4 | e11e5 | GGCACAGAGAAAGCAAACCACCCTGGGTGTTATAG | 44 |
| MLL-AF4 | e11e4 | GGCACAGAGAAAGCAAACCACCCTGGGTGTTATAG | 45 |
| PML-RARA | bcr1 (e6e3) | GCCACGTGGTTGCTGTTGGGCAGGAAGACCTCACTTCCTAT | 46 |
| PML-RARA | bcr3 (e3e3) | GAGCTGAGGTCCTGCAGGCGCACCTTGAACTCGTCGAAGC | 47 |
| PML-RARA | bcr2 (e6partial_e3) | TGGGGCTAGGCGGTCCATCCAGGTGGGGTGGTGAG | 48 |
| TEL-AML1 | e5e2 | GCATGGCGTGCTCTTCAGGCGGGGAGACAGAGACC | 49 |
| TEL-AML1 | e5e3 | GCATGGCGTGCTCTTCAGGCGGGGAGACAGAGACC | 50 |

Probes in Table 1 marked with (*) are mismatch junction probes that hybridize to the sequence across the gene fusion junction. Each has one, two or three mismatches shown underlined. These mismatches stop the probe from inappropriately hybridizing to a transcript which has only half of the relevant target sequence (for example, the wild-type transcript of one of the fusion genes), by lowering the amount of partial sequence complementarity so that stable hybridization can only occur with the true target. Such mismatches are only necessary in cases where the Tm of the sequence of one exon at the junction is high enough to be stable under standard hybridization conditions, and the sequence cannot simply be shortened because the shorter probe will not retain enough sequence specificity.

Probes in Table 1 marked with (+) are border probes. These probes do not hybridize to a sequence that crosses the gene fusion junction. The target sequence of these reporter probes is adjacent to the target sequence of the capture probes. Each probe only hybridizes to a sequence on one side of the gene fusion junction. The probe pair (capture and reporter) meets at the border of the fusion, with the capture probe sitting in the upstream exon and the reporter probe sitting fully in the downstream exon.

The unmarked sequences in Table 1 are probes with target sequences that cross the gene fusion junction, but do not have mismatches. The sequences of this class of probes are the exact reverse complement of the target sequence. Gaps in the sequence represent the fusion border; the probe sequence is actually contiguous across this gap. In these probe pairs, the reporter probe spans the fusion junction, and the capture probe sits adjacent in the upstream exon.

The disclosure also describes a panel of probes. These probes include probes for the detection of fusion genes from several gene families from various leukemia subtypes. The panel can contain probes for detection of 5, 6, 7, 8, 9, 10, 11, 12, 13, 14, 15, 16, 17, 18, 19, 20, 21, 22, 23, 24, 25 or more fusion genes. The genes can be from 1, 2, 3, 4, 5, 6, 7 or more gene families. The fusion genes can be present in any leukemia subtype including CML, AML or ALL.

The fusion events, or translocations, usually involve only one of the pair of each chromosome, leaving one intact copy, or "wild-type" copy, of each gene also present in the cell. The panel of probes can also include probes specific for mRNAs produced by the wild-type copies of the relevant genes, allowing the level of expression of the intact version of each gene involved in the translocation to be determined. The panel can include probes specific for 1, 2, 3, 4, 5, 6, 7, 8, 9, 10, 11, 12, 13, 14, 15 or more wild-type mRNAs.

The panel of probes can also include probes specific for mRNAs that are clinically relevant for the detection and diagnosis of leukemia. These markers for leukemia can include WT1, FLT3, BAALC, PRAME, MLLT11, ERG, MN1, RHAMM, HOX11L2, EVI1, N-RAS, RB1 and TP53.

The panel of probes can also include probes specific for housekeeper mRNAs. The results produced from these probes can be used as an internal control to estimate the amount of sample present in the assay. Probes for 1, 2, 3, 4 or more housekeeper mRNAs can be included in the panel.

An example of a panel of probes for the detection and/or diagnosis of leukemia or specific subtypes of leukemia is shown below in Table 2.

TABLE 2

| Gene Type/Fusion Gene Family | Fusion Gene Isoform | Target Sequence (5'-3') | SEQ ID NO: | Reporter Probe (5'-3') | SEQ ID NO: | Capture Probe (5'-3') | SEQ ID NO: |
|---|---|---|---|---|---|---|---|
| Housekeeper Genes | GUSB | UCUGUGGCCAACGAGCCUGCGUCCCACCUAGAAUCUGCUGGCUACUACUUGAAGAUGGUGAUCGCUCACACCAAAUCCUUGGA (SEQ ID NO:) | 51 | TCCAAGGATTTGGTGTGAGCGATCACCATCTTCAAGTAGTAGCCAGC | 52 | AGATTCTAGGTGGGACGCAGGCTCGTTGGCCACAGA | 53 |
| | TBP | CGCCGGCUGUUUAACUUCGCUUCCGCUGGCCCAUAGUGAUCUUUGCAGUGACCCAGCAGCAUCACUGUUUCUUGGCGUGUGAAGAUAACCCAAGGAAUUG | 54 | CAATTCCTTGGGTTATCTTCACACGCCAAGAAACAGTGATGCTGCTGGGT | 55 | CACTGCAAAGATCACTATGGGCCAGCGGAAGCGAAGTTAAACAGCCGGCG | 56 |
| | ABL1 | CUGUGAUUGACUUCAAUUGCUGACUUGUGGAGAUGCAGCGAAUGUGAAAAUCCCACGUAUAUGCCAUUUCCCUCUACGCUCGCUGACCGUUCUGGAAGAUC | 57 | GATCTTCCAGAACGGTCAGCGAGCGTAGAGGGAAATGGCATATACGTGGG | 58 | ATTTCACATTCGCTGCATCTCCACAAGTCAGCAATTGAAGTCAATCACAG | 59 |
| | BCR | CUGGGAGACAGGGUGAAGGGAGUGGUUUUAUGAACUUAACUUAGAGUCUAAAAGAUUUCUACUGGAUCACUUGUCAAGAUGCGCCCUCUCGGGGAGAA | 60 | TTCTCCCCAGAGAGGGCGCATCTTGACAAGTGATCCAGTAGAAATCTTTT | 61 | AGACTCTAAGTTAAGTTCATAAAAACCACTCCCTTCACCCTGTCTCCCAG | 62 |
| Leukemia Biomarkers | SOCS2 | GGAACGGCACUGUUCACCUUUAUCUGACCAAACCGCUCUACACGUCAGCACCAUCUCUGCAGCAUCUCUGUAGGCUCACCAUUAACAAAUGUACCGGUGC | 63 | GCACCGGTACATTTGTTAATGGTGAGCCTACAGAGATGCTGCAGAGATGG | 64 | TGCTGACGTGTAGAGCGGTTTGGTCAGATAAAGGTGAACAGTGCCGTTCC | 65 |
| | WT1 | UCAGAGAGCAAGGCAUCGGGGGUGAAUCUUGUCUAACAUUCCCGAGGUCAGCCAGGCUGCUAACCUGGAAAGCAGGAUGUAGUUCUGCCAGGCAACUUUU | 66 | AAAAGTTGCCTGGCAGAACTACATCCTGCTTTCCAGGTTAGCAGCCTGGC | 67 | TGACCTCGGGAATGTTAGACAAGATTCACCCCCGATGCCTTGCTCTCTGA | 68 |
| | FLT3 | AAAUGGAAAACCAGGACGCCCUGGUCUGCAUAUCUGAGAGCGUUCCAGAGCCGAUCGUGGAAUGGGUGCUUUGCGAUUCACAGGGGGAAAGCUGUAAAGA | 69 | TCTTTACAGCTTTCCCCCTGTGAATCGCAAAGCACCCATTCCACGATCGG | 70 | CTCTGGAACGCTCTCAGATATGCAGACCAGGGCGTCCTGGTTTTCCATTT | 71 |
| | BAALC | AAGAAUCACAAAGAACUGUGUCAACUAGCAGAGAGUCCAAGCAGAAGGGCAGAUGGACUUCUUCAGUGUCCUUCACGGCACUGGAUCCCAUCAAAGAACC | 72 | GGTTCTTTGATGGGATCCAGTGCCGTGAAGGACACTGAAGAAGTCCATCT | 73 | GCCCTTCTGCTTGGACTCTCTGCTAGTTGACACAGTTCTTTGTGATTCTT | 74 |
| | PRAME | GGUCUUUGAUGAGUGUGGGAUCACGGAUGAUCAGCUCCUUGCCCUCCUGCCUUCCCUGAGCCACUGCUCCCAGCUUACAACCUUAA | 75 | TTAAGGTTGTAAGCTGGGAGCAGTGGCTCAGGGAAGGCAGGAG | 76 | GGCAAGGAGCTGATCATCCGTGATCCCACACTCATCAAAGACC | 77 |
| | MLLT11 | GGAAUAGGACUAGGUUUAUUUACCCAUUGUGAGGGUAGAGAGGCGAGUCUGGAGGAGCAGGGAUUGGGAGAAGGGGUGGAAAAAUACUCUGAUUCUUAAA | 78 | TTTAAGAATCAGAGTATTTTTCCACCCCTTCTCCCAATCCCTGCTCCTC | 79 | AGACTCGCTCTCTACCCTCACAATGGGTAAATAAACCTAGTCCTATTCC | 80 |
| | ERG | GACCUCAUCAUUAUGUGGGGGCUUUGUUCUCCACAGGGUCAGGUAGUAAGAUGGCCUGUUUGGCUGCCACAAUCAGAAAUCACGCAGGCAUUUUGGGUAGG | 81 | CCTACCCAAAATGCCTGCGTGATTTCTGATTGTGGCAGCCAAGAAGGCCA | 82 | TCTCTTACCTGACCCTGTGGAGAACAAAGCCCCCACATAATGATGAGGTC | 83 |
| | MN1 | AGGGUGACGAACCAAGGAGCCGUCGACUCGCUGGAAUACAAUUACCCGGGCGAGGCGCCCUCGGGACAUUUUGACAUGUUUUCGCCCU | 84 | AGGGCGAAAACATGTCAAAATGTCCCGAGGGCGCCCTCGCCCCG | 85 | GTAATTGTATTCCAGCGAGTCGACGGCTCCTTGGTTCGTCACCCT | 86 |
| | RHAMM | UUGAAACCGGUAGGGAGUGAUAAUCCGCAUUCAGUUGUCGAGGAGUGCCAGUCACUUCAGUUUCUGGAGCUGGCCGUCAACAUGUCCUUUCCUAAGGCG | 87 | CGCCTTAGGAAAGGACATGTTGACGGCCAGCTCCAGAACTGAAGGTGAC | 88 | TGGCACTCCTCGACAACTGAATGCGGATTATCACTCCCTACCGGTTTCAA | 89 |
| | HOX11 | ACCACACAUCCCAGCCCAAUCCAGGUACGCACAGACAGGUUUUCACAUAAAUGCAGCCCAUUUCUCCAGAACCCAUUUGAGGGGUGGGGGGGUGUUAAUU | 90 | AATTAACACCCCCCACCCCTCAAATGGGTTCTGGAGAAATGGGCTGCAT | 91 | TTATGTGAAAACCTGTCTGTGCGTACCTGGATTGGGCTGGGATGTGTGGT | 92 |
| | HOX11L2 | GCGGCGCUCGCCAAGUCCCUCAAAAUGACGGACGCGCAGGUCAAGACCUGGUUCCAAAACCGGAGGACCAAGUGGCGG | 93 | CCGCCACTTGGTCCTCCGGTTTTGGAACCAGGTCTTGACC | 94 | TGCGCGTCCGTCATTTTGAGGGACTTGGCGAGCGCCGC | 95 |

TABLE 2-continued

| Gene Type/Fusion Gene Family | Fusion Gene Isoform | Target Sequence (5'-3') | SEQ ID NO: | Reporter Probe (5'-3') | SEQ ID NO: | Capture Probe (5'-3') | SEQ ID NO: |
|---|---|---|---|---|---|---|---|
| | EVI1 | GGGGCAGGACUAGGAAUAUGGACCAAAAGGAAGA UCGAAGUAGGUGAAAGUUUGGGCCUUAUGUGGG AGAGCAGAGGUCAAACCUGAAAGACCCCAGUU | 96 | AACTGGGGTCTTTC AGGTTTGACCTCTG CTCTCCCACATAAG GCCCAAAC | 97 | TTTTCACCTACTTC GATCTTCCTTTTGG TCCATATTCCTAGT CCTGCCCC | 98 |
| | N-RAS | CCCUGGUCCUGACUUCCCUGGAGGAGAAGUAUUC CUGUUGCUGUCUUCAGUCUCACAGAGAAGCUCCU GCUACUUCCCCAGCUCUCAGUAGUUUAGUAC | 99 | GTACTAAACTACTG AGAGCTGGGGAAGT AGCAGGAGCTTCTC TGTGAGAC | 100 | TGAAGACAGCAAC AGGAATACTTCTCC TCCAGGGAAGTCA GGACCAGGG | 101 |
| | RB1 | CCUAUCUCCGGCUAAAUACACUUUGUGAACGCCU UCUGUCUGAGCACCCAGAAUUAGAACAUAUCAUC UGGACCCUUUUCCAGCACACCCUGCAGAAUGA | 102 | TCATTCTGCAGGGT GTGCTGGAAAAGGG TCCAGATGATATGT TCTAATTC | 103 | TGGGTGCTCAGACA GAAGGCGTTCACA AAGTGTATTTAGCC GGAGATAGG | 104 |
| | TP53 | CAGGGCUCACUCCAGCCACCUGAAGUCCAAAAAG GGUCAGUCUACCUCCCGCCAUAAAAAACUCAUGU UCAAGACAGAAGGGCCUGACUCAGAC | 105 | GTCTGAGTCAGGCC CTTCTGTCTTGAAC ATGAGTTTTTATG GCGGGAGG | 106 | TAGACTGACCCTTT TTGGACTTCAGGTG GCTGGAGTGAGCCC TG | 107 |
| Wild Type Transcripts | PML | GAGGUGGGGCUGCAGCACUUCCUCAGCUUUCUGA GCUCCAUGCGCCGCCCUAUCUUGGCCUGCUACAA GCUGUG | 108 | CACAGCTTGTAGCA GGCCAAGATAGGGC GGCGCATGGAG | 109 | CTCAGAAAGCTGA GGAAGTGCTGCAG CCCCACCTC | 110 |
| | RARA | CUGGGGCCCAUCUAGGAGUGGCAUCUUUUUUGU GCCCUGAAGGCCAGCUCUGGACCUUCCCAGGAAA AGUGCCAG | 111 | CTGGCACTTTTCCT GGGAAGGTCCAGAG TCGGCCTT | 112 | CAGGGCACCAAAA AAGATGCCACTCCT AGATGGGCCCCAG | 113 |
| | ETO (RUNX1) | CAGCCAUGAAGAACCAGGUUGCAAGAUUUAAUGA CCUCAGGUUUGUCGGUCGAAGUGGAAGAGGGAAA AGCUUCACUCUGACCAUCACUGUCUUCA | 114 | TGAAGACAGTGATG GTCAGAGTGAAGCT TTTCCCTCTTCCAC TTCG | 115 | ACCGACAAACCTG AGGTCATTAAATCT TGCAACCTGGTTCT TCATGGCTG | 116 |
| | ETV6 (TEL) | CGCCACUACUACAAACUAAACAUUAUCAGGAAGG AGCAGGACAAAGGCUUUUGUUCAGGUUUAUGAA AACCCCAGAUGAAAUCAUGAGUG | 117 | CACTCATGATTTCA TCTGGGGTTTTCAT AAACCTGAACAAA GCCTTTGT | 118 | CCTGGCTCCTTCCT GATAATGTTTAGTT TGTAGTAGTGGCG | 119 |
| | TCF3 (E2A) | CUUGGAGCAGCAAGUGCGAGAGCGGAACCUGAAU CCCAAAGCAGCCUGUUUGAAACGGCGAGAAGAGG AAAAG | 120 | CTTTTCCTCTTCTC GCCGTTTCAAACAG GCTGCTTTGG | 121 | GATTCAGGTTCCGC TCTCGCACTTGCTG CTCCAAG | 122 |
| | PBX1 | CGGGAGGAAGCAGGACAUUGGAGACAUUUUACAG CAAAUUAUGACCAUCACAGACCAGAGUUUGGAUG AGGCGCAGGCCAGAAAACAUGCUUUAAACUGC | 123 | GCAGTTTAAAGCAT GTTTTCTGGCCTGC GCCTCATCCAAACT CTGGTCTG | 124 | TGATGGTCATAATT TGCTGTAAAATGTC TCCAATGTCCTGCT TCCTCCCG | 125 |
| | CBFB | CAGUGUUGCCCAGGCUGGUCUCGAACUCCUGGCA UCAAGCGAUCCUCCUGCCUUAGCCUCCCAGAGUA CUG | 126 | CAGTACTCTGGGAG GCTAAGGCAGGAGG ATCGCTTG | 127 | ATGCCAGGAGTTCG AGACCAGCCTGGG CAACACTG | 128 |
| | MYH11 | CUGCUAGAAAAAUCACGGGCAAUUCGCCAAGCCA GAGACGAGAGGACAUUCCACAUCUUUUUACUACAU GAUUGCUGGAGCCAAGGAGAAGAUGAGAAGUG | 129 | CACTTCTCATCTTC TCCTTGGCTCCAGC AATCATGTAGTAAA AGATGTGG | 130 | AATGTCCTCTCGTC TCTGGCTTGGCGAA TTGCCCGTGATTTT TCTAGCAG | 131 |
| | MLL | CAAAAUGAGUGGACACAUGUAAAAUUGUGCUUUGU GGUCAGCGGAAGUGUUUGAAGAUGAUGACGGAUC ACUAAAGAAUGUGCAUAUGGCUGUGAUCAG | 132 | CTGATCACAGCCAT ATGCACATTCTTTA GTGATCCGTCATCA TCTTCA | 133 | AACACTTCCGCTGA CCACAAAGCACAA TTTACATGTGTCCA CTCATTTTG | 134 |
| | AFF1 (AF4) | UGAACUGAAACCACUGCCGGAGGACUAUCGACAG CAGACCUUUGAAAAAACAGACUUGAAAGUGCCUG CCAAAGCCAAGCUCACCAAACUGAAGAUGCCU | 135 | AGGCATCTTCAGTT TGGTGAGCTTGGCT TTGGCAGGCACTTT CAAGTCTG | 136 | TTTTTTCAAAGGTC TGCTGTCGATAGTC CTCCGGCAGTGGTT TCAGTTCA | 137 |
| BCR-ABL | b2a2 | AACUCGUGUGUGAAACUCCAGACUGUCCACAGCA UUCCGCUGACCAUCAAUAAGGAAGAAGCCCUUCA GCGGCCA | 138 | TGGCCGCTGAAGGG CTTCTTCCTTATTG TAGGTCA | 139 | GCGGAATGCTGTGG ACAGTCTGGAGTTT CACACACGAGTT | 140 |
| | b3a2 | GUCUCCGGGGCUCUAUGGGUUUCUGAAUGUCAUC GUCCACUCAGCCACUGGAUUUAAGCAGAGUUCAA AAGCCCUUCAGCGGCCA | 141 | TGGCCGCTGAAGGG CTTTTGAACTCTGC TTAAATC | 142 | CAGTGGCTGAGTGG ACGATGACATTCAG AAACCCATAGAGC CCCGGAGAC | 143 |

TABLE 2-continued

| Gene Type/Fusion Gene Family | Fusion Gene Isoform | Target Sequence (5'-3') | SEQ ID NO: | Reporter Probe (5'-3') | SEQ ID NO: | Capture Probe (5'-3') | SEQ ID NO: |
|---|---|---|---|---|---|---|---|
| | e1a2 | CGCAAGACCGGGCAGAUCUGGCCCAACGAUGGCG AGGGCGCCUUCCAUGGAGACGCAGAAGCCCUUCA GCGGCCA | 144 | TGGCCGCTGAAGGG CTTCTGCATCTCCA TGGAAGG | 145 | CGCCCTCGCCATCG TTGGGCCAGATCTG CCCGGTCTTGCG | 146 |
| | e19a2 | CGUGUCCGGUGUGGCCACGGACAUCCAGGCACUG AAGGCAGCCUUCGACGUCAAAGCCCUUCAGCGGC CA | 147 | TGGCCGCTGAAGGG CTTTGACGTCGAAA GCTGCCT | 148 | TCAGTGCCTGGATG TCCGTGGCCACACC GGACACG | 149 |
| | b3a3 | UGGGUUUCUGAAUGUCAUCGUCCACUCAGCCACU GGAUUUAAGCAGAGUUCAAGUGAAAAGCUCCGGG UC | 150 | GACCCGGAGCTTTT CACTTGAACTCTGC TTAAATC | 151 | CAGTGGCTGAGTGG ACGATGACATTCAG AAACCCA | 152 |
| | b2a3 | GUGUGUGAAACUCCAGACUGUCCACAGCAUUCCG CUGACCAUCAAUAAGGAAGGUGAAAAGCUCCGGG UC | 153 | GACCCGGAGCTTTT CACCTTCCTTATTG ATGGTCA | 154 | GCGGAATGCTGTGG ACAGTCTGGAGTTT CACACAC | 155 |
| | e1a3 | CGCAAGACCGGGCAGAUCUGGCCCAACGAUGGCG AGGGCGCCUUCCAUGGAGACGCAGGUGAAAAGCU CCGGGUC | 156 | GACCCGGAGCTTTT CACCTGCATCTCCA TGGAAGG | 157 | CGCCCTCGCCATCG TTGGGCCAGATCTG CCCGGTCTTGCG | 158 |
| AML-ETO | | CUACCACAGAGCCAUCAAAAUCACAGUGGAUGGG CCCCGAGAACCUCGAAAUCUACUGAGAAGCACU CCACAAUGCCAGACUCACCUGUGGAUGUGAAG | 159 | CTTCACATCCACAG GTGAGTCTGGCATT GTGGAGTGCTTCTC AGTACGAT | 160 | TTCGAGGTTCTCGG GGCCCATCCACTGT GATTTTGATGGCTC TGTGGTAG | 161 |
| CBFb-MYH11 | e5e12 | GAAAUGGAGGUGAGAGUUUCACAGCUGCUGGCAG UAACUGGUCCAUGAGCUGGAGAAGUCCAAGCGGG CCCUGGA | 162 | TCCAGGGCCCGCTT GGACTTCTCCAGCT CATGGAC | 163 | CAGTTACTGCCAGC AGCTGTGAAACTCT CACCTCCATTTC | 164 |
| | e5e8 | GAAAUGGAGGUGAGAGUUUCACAGCUGCUGGCAG UAACUGAAUGAAGUUGAGAGCGUCACAGGGAUGC UUAACGAGGCCG | 165 | CGGCCTCGTTAAGC ATCCCTGTGACGCT CTCAACTTCATT | 166 | CAGTTACTGCCAGC AGCTGTGAAACTCT CACCTCCATTTC | 167 |
| | e5e7 | GAAAUGGAGGUGAGAGUUUCACAGCUGCUGGCAG UAACUGGCCAAGGCGAACCUAGACAAGAAUAAGC AGACGCU | 168 | AGCGTCTGCTTATT CTTGTCTAGGTTCG CCTTGGC | 169 | CAGTTACTGCCAGC AGCTGTGAAACTCT CACCTCCATTTC | 170 |
| E2A-PBX1 | e13-insertion-n27-e2 | ACCCUCCCUGACCUGUCUCGGCCUCCCGACUCCU ACAGUGAUGAAAGUGUUCGGUCACCUGGAACCUU UU | 171 | AAAAGGTTCCAGGT GACCGAACACTTTC ATCACTG | 172 | TAGGAGTCGGGAG GCCGAGACAGGTC AGGGAGGGT | 173 |
| | e13e2 | AGCCAGCCAGGCACCCUCCCUGACCUGUCUCGGC CUCCCGACUCCUACAGUGUUUUGAGUAUCCGAGG A | 174 | TCCTCGGATACTCA AAACACTGTAGGAG TCGGGAG | 175 | GCCGAGACAGGTC AGGGAGGGTGCCT GGCTGGCTG | 176 |
| MLL-AF4 | e8e7 | CAAAACCACUCCUAGUGAGCCCAAGAAAAAGCAG CCUCCACCACCAGAAUCAGAACAAUAUGAUACAU CU | 177 | AGATGTATCATATT GTTCTGATTCTGGT GGTGGAG | 178 | GCTGCTTTTTCTTG GGCTCACTAGGAGT GGTTTTG | 179 |
| | e9e5 | AAAAAGUGGCUCCCCGCCCAAGUAUCCCUGUAAA ACAAAAACCAAAAGAAAAGGAAAUGACCCAUUCA UG | 180 | CATGAATGGGTCAT TTCCTTTTCTTTTG GTTTTTG | 181 | TTTTACAGGGATAC TTGGGCGGGGAGC CACTTTTT | 182 |
| | e9e4 | AAAAAGUGGCUCCCCGCCCAAGUAUCCCUGUAAA ACAAAAACCAAAAGAAAAGCAGACCUACUCCAAU GA | 183 | TCATTGGAGTAGGT CTGCTTTTCTTTTG GTTTTTG | 184 | TTTTACAGGGATAC TTGGGCGGGGAGC CACTTTTT | 185 |
| | e10e5 | CUAAGCAAAAAAUUCCAGCAGAUGGAGUCCACAG GAUCAGAGUGGACUUUAAGGAAAUGACCCAUUCA UG | 186 | CATGAATGGGTCAT TTCCTTAAAGTCCA CTCTGAT | 187 | CCTGTGGACTCCAT CTGCTGGAATTTTT TGCTTAGC | 188 |
| | e10e4 | CUAAGCAAAAAAUUCCAGCAGAUGGAGUCCACAG GAUCAGAGUGGACUUUAAGCAGACCUACUCCAAU GA | 189 | TCATTGGAGTAGGT CTGCTTAAAGTCCA CTCTGAT | 190 | CCTGTGGACTCCAT CTGCTGGAATTTTT TGCTTAG | 191 |
| | e11e5 | CUAUAACACCCAGGGUGGUUUGCUUUCUCUGUGC CAGUAGUGGGCAUGUAGAGGAAAUGACCCAUUCA UG | 192 | CATGAATGGGTCAT TTCCTATACATGCC CACTACT | 193 | GGCACAGAGAAAG CAAACCACCCTGGG TGTTATAG | 194 |
| | e11e4 | CUAUAACACCCAGGGUGGUUUGCUUUCUCUGUGC CAGUAGUGGGCAUGUAGAGCAGACCUACUCCAAU GA | 195 | TCATTGGAGTAGGT CTGCTATACATGCC CACTACT | 196 | GGCACAGAGAAAG CAAACCACCCTGGG TGTTATAG | 197 |

TABLE 2-continued

| Gene Type/Fusion Gene Family | Fusion Gene Isoform | Target Sequence (5'-3') | SEQ ID NO: | Reporter Probe (5'-3') | SEQ ID NO: | Capture Probe (5'-3') | SEQ ID NO: |
|---|---|---|---|---|---|---|---|
| PML-RARA | bcr1 (e6e3) | AUAGGAAGUGAGGUCUUCCUGCCCAACAGCAACC ACGUGGCCAGUGGCGCCGGGGAGGCAGCCAUUGA GACCCAGA | 198 | TCTGGGTCTCAATG GCTGACTCCCAAGC GCCACTG | 199 | GCCACGTGGTTGCT GTTGGGCAGGAAG ACCTCACTTCCTAT | 200 |
| | bcr3 (e3e3) | GGCUUCGACGAGUUCAAGGUGCGCCUGCAGGACC UCAGCUCUUGCAUCACCCAGGGGAAAGCCAUUGA GACCCAGA | 201 | TCTGGGTCTCAATG GCTTTCCACTGGGT GATGCAA | 202 | GAGCTGAGGTCCTG CAGGCGCACCTTGA ACTCGTCGAAGC | 203 |
| | bcr2 (e6partial_e3) | CUCACCACCCCACCUGGAUGGACCGCCUAGCCCC AGGAGCCCCGUCAUAGGAACCAUUGAGACCCAGA GC | 204 | GCTCTGGGTCTCAA TGGTTCCTATGACG GGACTCC | 205 | TGGGGCTAGGCGGT CCATCCAGGTGGGG TGGTGAG | 206 |
| TEL-AML1 | e5e2 | GGUCUCUGUCUCCCCGCCUGAAGAGCACGCCAUG CCCAUUGGGAGAAUAGCAGGUGGUGGCCCUAGGG GA | 207 | TCCCCTAGGGCCAC CACCTGCTATTCTC ACAATGG | 208 | GCATGGCGTGCTCT TCAGGCGGGGAGA CAGAGACC | 209 |
| | e5e3 | GGUCUCUGUCUCCCCGCCUGAAGAGCACGCCAUG CCCAUUGGGAGAAUAGCAGGGAAAAGCUUCACUC UG | 210 | CAGAGTGAAGCTTT TCCCTGCTATTCTA CCAATGG | 211 | GCATGGCGTGCTCT TCAGGCGGGGAGA CAGAGACC | 212 | nCounter® Analysis System Overview

The basis of the nCounter® Analysis system is the unique code assigned to each gene to be assayed (International Patent Application No. PCT/US2008/059959 and Geiss et al. Nature Biotechnology. 2008. 26(3): 317-325; the contents of which are each incorporated herein by reference in their entireties). The code is composed of an ordered series of colored fluorescent spots which create a unique barcode for each target to be assayed. A pair of probes is designed for each target, a biotinylated capture probe and a reporter probe carrying the fluorescent barcode.

Specific reporter and capture probes are synthesized for each target. Briefly, sequence-specific DNA oligonucleotide probes are attached to code-specific reporter molecules. Capture probes are made by ligating a second sequence-specific DNA oligonucleotide for each target to a universal oligonucleotide containing biotin. Reporter and capture probes are all pooled into a single hybridization mixture, the "probe library".

The expression levels of all targets are measured in a single multiplexed hybridization reaction. The sample is combined with the probe library, and specific hybridization of the reporter and the capture probes to their target molecules occurs in solution. After hybridization, the tripartite hybridized complexes are purified in a two-step procedure using magnetic beads linked to oligonucleotides complementary to universal sequences present on the capture and reporter probes. This dual purification process allows the hybridization reaction to be driven to completion with a large excess of target-specific probes, as they are ultimately removed, and, thus, do not interfere with binding and imaging of the sample. All post hybridization steps are handled robotically on a custom liquid-handling robot (Prep Station, NanoString Technologies).

Purified reactions are deposited by the Prep Station into individual flow cells of a sample cartridge, bound to a streptavidin-coated surface via the capture probe, electrophoresed to elongate the reporter probes, and immobilized. After processing, the sample cartridge is transferred to a fully automated imaging and data collection device (Digital Analyzer, NanoString Technlogies). The expression level of a target is measured by imaging each sample and counting the number of times the code for that target is detected. For each sample, typically 600 fields-of-view (FOV) are imaged (1376×1024 pixels) representing approximately 10 mm$^2$ of the binding surface. Typical imaging density is 100-1200 counted reporters per field of view depending on the degree of multiplexing, the amount of RNA, and overall target expression levels. Data is output in simple spreadsheet format listing the number of counts per target, per sample.

In certain embodiments the analysis system used herein also used a reference sample as a control. The reference samples are known quantities of nucleic acid fragments with sequences that correspond to one or more fusion genes. For example, a reference sample with a sequence corresponding to a specific fusion gene is used with a nanoreporter with a target-specific probe that specifically binds to a sequence on the same fusion gene. When multiple nanoreporters are used for multiple fusion genes, the reference sample may contain multiple target nucleic acids which correspond to the sequences that the target specific probes of the nanoreporters specifically bind to.

Kits

The present disclosure also describes kits useful for detecting and diagnosing leukemia. These kits comprise a set of probes described above. For example, the kit may include any number of probes described in Table 2, above. The kit may further comprise a computer readable medium.

In another embodiment, the kit includes probes that may be provided in a lyophilized or reconstituted form, or may be provided as a set of nucleotide sequences. In one embodiment, the probes are provided in a microplate format, where each probe set occupies a well (or multiple wells, as in the case of replicates) in the microplate. The kit may further comprise reagents and instructions sufficient for the detection of the various target sequences described above.

EXAMPLE

Figure 1B:
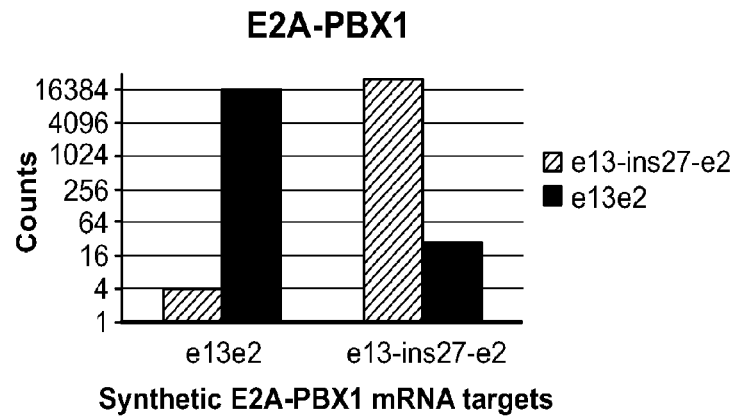
FIG. 1B is a bar graph showing counts for probes for the E2A-PBX1 gene fusion when exposed to gene fragments of the E2A-PBX1 gene fusion and non-specific targets.
Figure 1C:
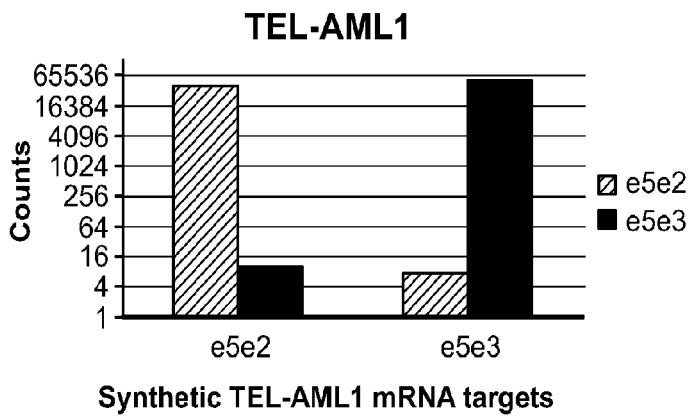
FIG. 1C is a bar graph showing counts for probes for the TEL-AML1 gene fusion when exposed to gene fragments of the TEL-AML1 gene fusion and non-specific targets.
Figure 1D:
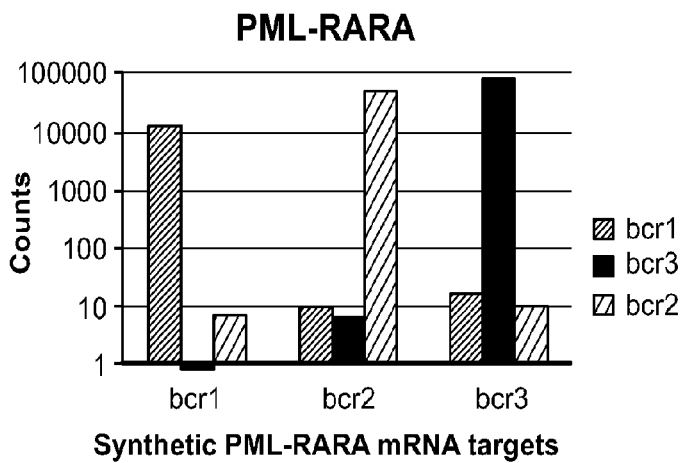
FIG. 1D is a bar graph showing counts for probes for the PML-RARA gene fusion when exposed to gene fragments of the PML-RARA gene fusion and non-specific targets.

Example 1. Functional Performance of Fusion Probes Showing Specificity for Fusion Gene Isoforms on Synthetic Gene Fragments A multiplexed collection of nanoreporters containing probes to all the isoforms of BCR-ABL, E2A-PBX1, TEL- AML1 and PML-RARA listed in Table 1 was used to detect synthetic transcripts of sequences corresponding with each of these gene fusions. An nCounter® leukemia fusion gene expression assay was performed as described below, and some of the resulting counts for each probe are shown in log 2 scale in FIG. 1. Cross-hybridization for each individual probe to non-specific targets was below 1%.

The leukemia fusion gene expression assay was run on the nCounter® Analysis system (NanoString). Each sample was hybridized to the multiplexed nanoreporters in solution, followed by post-hybidization sample processing on the nCounter® Prep Station and data collection on the nCounter® Digital Analyzer.

Hybridization Protocol

Each hybridization reaction contained the following components: 10 µL Reporter CodeSet, 10 µL hybridization buffer, 5 µL synthetic RNA target to a final concentration of 1 µM, and 5 µL Capture ProbeSet.

Aliquots of both the Reporter CodeSet and Capture ProbeSet reagent were removed from the freezer and thawed on ice. The aliquots were inverted several times to mix well. The reagent was briefly spun down at <1000 rpm.

A master mix was created containing 130 µL of the Reporter CodeSet and 130 µL of hybridization buffer by adding the hybridization buffer to the tube containing the Reporter CodeSet. The master mix was inverted to mix and spun down, and 20 µL of master mix was added to each of 12 tubes.

Samples of synthetic target transcripts were denatured 85° C. for 5 minutes and quick-cooled on ice before being added to each tube and mixed. Targets were added to a final concentration of 1 µM.

The thermocycler was pre-heated to 65° C. 5 µL of Capture ProbeSet were added to each tube and mixed well before placing immediately at 65° C. Hybridization assays were incubated at 65° C. overnight.

Hybridizations were left at 65° C. until ready for processing. Once removed from 65° C., the assay proceeded immediately to post-hybridization processing on the nCounter® Prep Station.

Post-Hybridization Processing and Data Collection

After hybridization, an automated protocol on the nCounter® Prep Station was used to wash away excess probes and bind the captured probe/target complexes onto a cartridge, and then stretch and immobilize the captured nanoreporters in preparation for imaging. The purification procedure involved a two-step magnetic beadbased affinity purification. Magnetic beads derivatized with short nucleic acid sequences that were complementary to the Capture Probes and the Reporter Probes were used sequentially. First, the hybridization mixture containing target/probe complexes was allowed to bind to magnetic beads complementary to sequences on the Capture Probe. Wash steps were performed to remove excess Reporter Probes. After washing, the Capture Probes and target/probe complexes were eluted off the beads and hybridized to magnetic beads complementary to sequences on the Reporter Probe. An additional wash was performed to remove excess Capture Probes. Finally, the purified Capture Probe/target/Reporter Probe complexes were eluted off the beads and the captured nanoreporters were bound, stretched and immobilized on a cartridge for data collection.

Automated data collection was carried out in the nCounter® Digital Analyzer. Digital images of 600 fields of view of the bound nanoreporters were processed and the counts for each nanoreporter barcode were tabulated in a comma separated value (CSV) format.

Figure 2A:
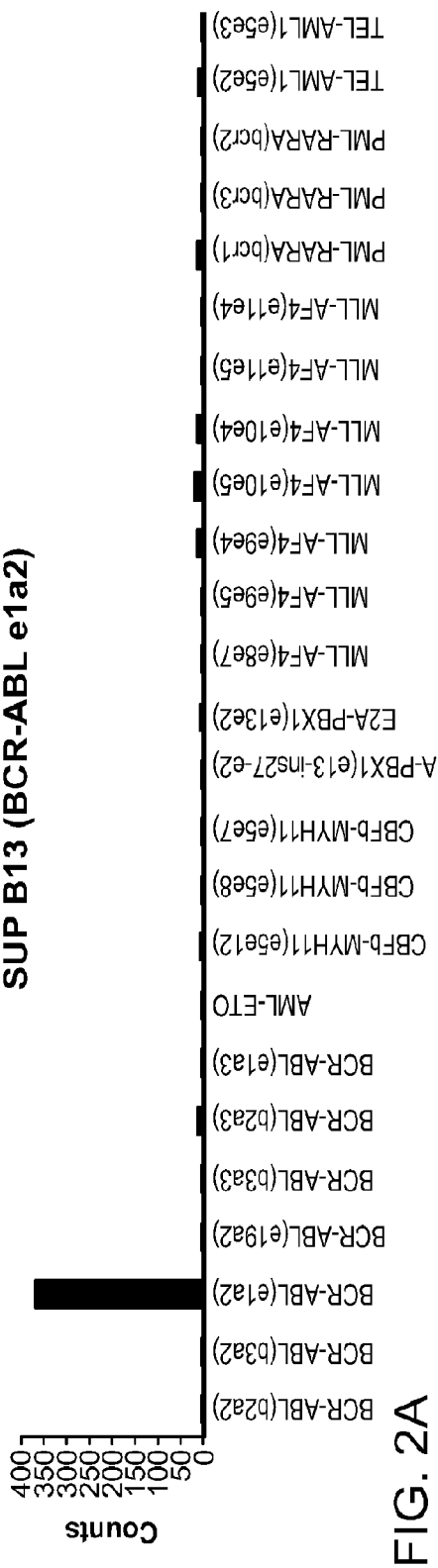
FIG. 2A is a bar graph showing the relative expression of various gene fusions in the SUP B13 cell line.
Figure 2B:
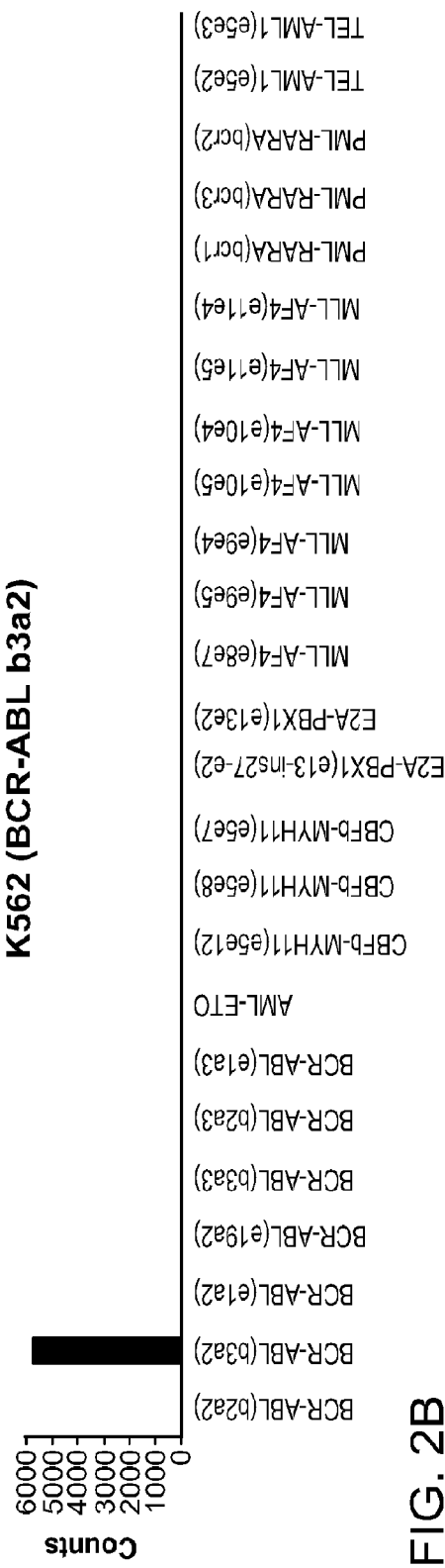
FIG. 2B is a bar graph showing the relative expression of various gene fusions in the K562 cell line.
Figures 2C, 2D:
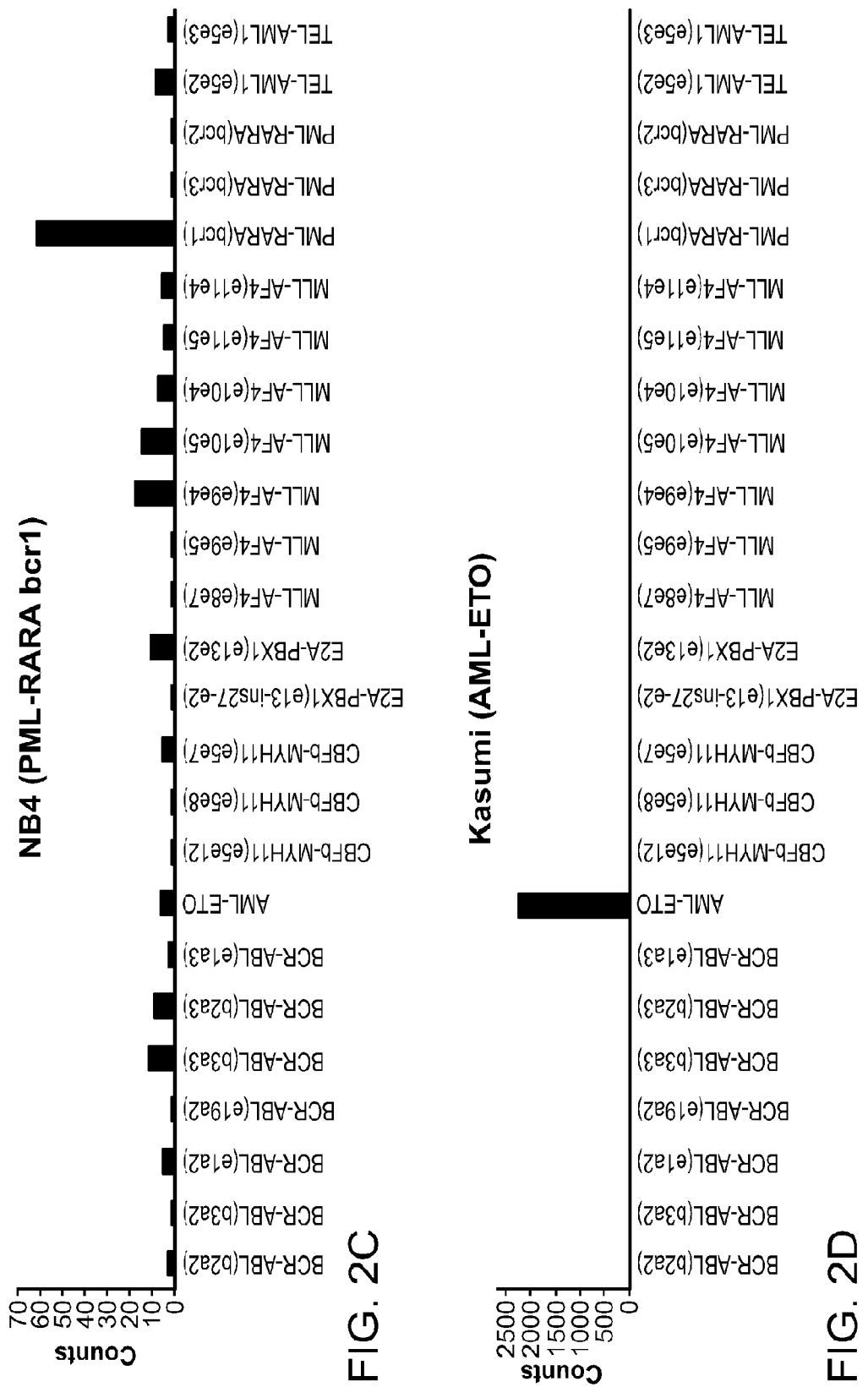
FIG. 2C is a bar graph showing the relative expression of various gene fusions in the NB4 cell line.
FIG. 2D is a bar graph showing the relative expression of various gene fusions in the Kasumi cell line.

Example 2. Leukemia Fusion Gene Panel Tested on Total RNA Isolated from Cell Lines FIGS. 2A-F show results from a Leukemia Fusion Gene Panel tested on total RNA isolated from 5 cell lines. The assay was performed as described in Example 1 with 100 ng of input RNA. Probes included in the CodeSet identified their respective targets expressed in the different cell lines: the BCR-ABL e1a2 isoform expressed in cell line SUP B13 (A), the BCR-ABL b3a2 isoform expressed in cell line K562 (B), the PML-RARA bcrl isoform expressed in cell line NB4 (C), the AML-ETO fusion gene transcript expressed in the Kasumi cell line (D), the BCR-ABL b2a2 isoform expressed in cell line KCL-22 (E) and the MLL-AF4 e9e5 isoform expressed in cell line MV4-11 (F).

OTHER EMBODIMENTS

While the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this disclosure has been particularly shown and described with references to preferred embodiments thereof, it will be understood by those skilled in the art that various changes in form and details may be made therein without departing from the scope of the disclosure encompassed by the appended claims.

What is claimed is:

1. A composition for the diagnosis of leukemia comprising a probe pair comprising a first probe and a second probe, said first probe comprising a complex comprising:
   (a) a first molecule, comprising:
      (i) a first label attachment region to which are attached one or more label monomers that emit light constituting a first signal;
      (ii) a second label attachment region, which is non-overlapping with the first label attachment region, to which are attached one or more label monomers that emit light constituting a second signal; and
   (b) a first target-specific sequence attached to the first molecule,
      wherein at least one of the first probes comprises a first target-specific sequence comprising a sequence selected from the group consisting of SEQ ID NO: 139, 142, 145, 148, 151, 154, and 157,
said second probe comprising a second molecule, comprising
   (i) a second target-specific sequence,
      wherein at least one of the second probes comprises a second target-specific sequence comprising a sequence selected from the group consisting of SEQ ID NO: 140, 143, 146, 149, 152, 155, and 158; and
   (ii) an affinity tag, wherein the affinity tag is biotin;
wherein the first target-specific sequence and the second target-specific sequence bind to different regions of the same target molecule,
wherein the target molecule is a fusion gene or mRNA transcribed from said fusion gene,
wherein the fusion gene is the result of the fusion of two or more genes in a patient at the onset of or during progression of leukemia and wherein when said probe pair is bound to its target molecule, the identity of the first and second signals and their locations relative to each other constitute at least part of a code that identifies the target molecule,
wherein the fusion gene comprises the fusion of at least a portion of a first gene and at least a portion of a second gene, and
wherein the first target-specific sequence hybridizes to a portion of the first gene and the second target-specific sequence hybridizes to a portion of the second gene.

2. The composition of claim 1, wherein the first target-specific sequence hybridizes to a sequence adjacent to a sequence that the second target-specific sequence hybridizes to on the fusion gene.

3. The composition of claim 1, wherein the first target-specific sequence hybridizes to a portion of the first gene and a portion of the second gene.

4. The composition of claim 3, wherein the first target-specific sequence hybridizes to a sequence adjacent to a sequence that the second target-specific sequence hybridizes to on the fusion gene.

5. The composition of claim 1, wherein the second target-specific sequence hybridizes to a portion of the first gene and a portion of the second gene.

6. The composition of claim 5, wherein the first target-specific sequence hybridizes to a sequence adjacent to a sequence that the second target-specific sequence hybridizes to on the fusion gene.

7. The composition of claim 5, wherein at least one of the target-specific sequences comprises a region with one or more mismatches to the target of the target-specific sequence.

8. The composition of claim 1, wherein the leukemia is selected from the group consisting of chronic myelogenous leukemia, acute myeloid leukemia and acute lymphoblastic leukemia.

9. The composition of claim 1, wherein each of said label monomers are selected from the group consisting of a fluorochrome moiety, a fluorescent moiety, a dye moiety or a chemiluminescent moiety.

10. The composition of claim 9, wherein each of said label monomers comprise a fluorescent moiety.

11. The composition of claim 9, wherein the unique label for each target-specific probe is composed of 4 label monomers.

12. The composition of claim 9, wherein the unique label for each target-specific probe is composed of 5 label monomers.

* * * * *

SEQUENCE LISTING

<160> NUMBER OF SEQ ID NOS: 212

<210> SEQ ID NO 1
<211> LENGTH: 35
<212> TYPE: DNA
<213> ORGANISM: Homo sapiens

<400> SEQUENCE: 1
tggccgctga agggcttctt ccttattgat ggtca                              35

<210> SEQ ID NO 2
<211> LENGTH: 35
<212> TYPE: DNA
<213> ORGANISM: Homo sapiens

<400> SEQUENCE: 2
tggccgctga agggcttttg aactctgctt aaatc                              35

<210> SEQ ID NO 3
<211> LENGTH: 35
<212> TYPE: DNA
<213> ORGANISM: Homo sapiens

<400> SEQUENCE: 3
tggccgctga agggcttctg catctccatg gaagg                              35

<210> SEQ ID NO 4
<211> LENGTH: 35
<212> TYPE: DNA
<213> ORGANISM: Homo sapiens

<400> SEQUENCE: 4
tggccgctga agggctttga cgtcgaaagc tgcct                              35

<210> SEQ ID NO 5
<211> LENGTH: 35
<212> TYPE: DNA
<213> ORGANISM: Homo sapiens

<400> SEQUENCE: 5
gacccggagc ttttcacttg aactctgctt aaatc                              35

<210> SEQ ID NO 6
<211> LENGTH: 35
<212> TYPE: DNA
<213> ORGANISM: Homo sapiens

<400> SEQUENCE: 6
gacccggagc ttttcacctt ccttattgat ggtca                              35

<210> SEQ ID NO 7
<211> LENGTH: 35
<212> TYPE: DNA
<213> ORGANISM: Homo sapiens

<400> SEQUENCE: 7
gacccggagc ttttcacctg catctccatg gaagg                              35

<210> SEQ ID NO 8
<211> LENGTH: 50
<212> TYPE: DNA
<213> ORGANISM: Homo sapiens

<400> SEQUENCE: 8
cttcacatcc acaggtgagt ctggcattgt ggagtgcttc tcagtacgat              50

<210> SEQ ID NO 9
<211> LENGTH: 35
<212> TYPE: DNA
<213> ORGANISM: Homo sapiens

```
<400> SEQUENCE: 9
tccagggccc gcttggactt ctccagctca tggac                                    35

<210> SEQ ID NO 10
<211> LENGTH: 40
<212> TYPE: DNA
<213> ORGANISM: Homo sapiens

<400> SEQUENCE: 10
cggcctcgtt aagcatccct gtgacgctct caacttcatt                               40

<210> SEQ ID NO 11
<211> LENGTH: 35
<212> TYPE: DNA
<213> ORGANISM: Homo sapiens

<400> SEQUENCE: 11
agcgtctgct tattcttgtc taggttcgcc ttggc                                    35

<210> SEQ ID NO 12
<211> LENGTH: 35
<212> TYPE: DNA
<213> ORGANISM: Homo sapiens

<400> SEQUENCE: 12
aaaaggttcc aggtgaccga acactttcat cactg                                    35

<210> SEQ ID NO 13
<211> LENGTH: 35
<212> TYPE: DNA
<213> ORGANISM: Homo sapiens

<400> SEQUENCE: 13
tcctcggata ctcaaaacac tgtaggagtc gggag                                    35

<210> SEQ ID NO 14
<211> LENGTH: 35
<212> TYPE: DNA
<213> ORGANISM: Homo sapiens

<400> SEQUENCE: 14
agatgtatca tattgttctg attctggtgg tggag                                    35

<210> SEQ ID NO 15
<211> LENGTH: 35
<212> TYPE: DNA
<213> ORGANISM: Homo sapiens

<400> SEQUENCE: 15
catgaatggg tcatttcctt ttcttttggt ttttg                                    35

<210> SEQ ID NO 16
<211> LENGTH: 35
<212> TYPE: DNA
<213> ORGANISM: Homo sapiens

<400> SEQUENCE: 16
tcattggagt aggtctgctt ttcttttggt ttttg                                    35

<210> SEQ ID NO 17
<211> LENGTH: 35
<212> TYPE: DNA
```

```
<400> SEQUENCE: 17
catgaatggg tcatttcctt aaagtccact ctgat                              35

<210> SEQ ID NO 18
<211> LENGTH: 35
<212> TYPE: DNA
<213> ORGANISM: Homo sapiens

<400> SEQUENCE: 18
tcattggagt aggtctgctt aaagtccact ctgat                              35

<210> SEQ ID NO 19
<211> LENGTH: 35
<212> TYPE: DNA
<213> ORGANISM: Homo sapiens

<400> SEQUENCE: 19
catgaatggg tcatttccta tacatgccca ctact                              35

<210> SEQ ID NO 20
<211> LENGTH: 35
<212> TYPE: DNA
<213> ORGANISM: Homo sapiens

<400> SEQUENCE: 20
tcattggagt aggtctgcta tacatgccca ctact                              35

<210> SEQ ID NO 21
<211> LENGTH: 35
<212> TYPE: DNA
<213> ORGANISM: Homo sapiens

<400> SEQUENCE: 21
tctgggtctc aatggctgac tcccaagcgc cactg                              35

<210> SEQ ID NO 22
<211> LENGTH: 35
<212> TYPE: DNA
<213> ORGANISM: Homo sapiens

<400> SEQUENCE: 22
tctgggtctc aatggctttc cactgggtga tgcaa                              35

<210> SEQ ID NO 23
<211> LENGTH: 35
<212> TYPE: DNA
<213> ORGANISM: Homo sapiens

<400> SEQUENCE: 23
gctctgggtc tcaatggttc ctatgacggg actcc                              35

<210> SEQ ID NO 24
<211> LENGTH: 35
<212> TYPE: DNA
<213> ORGANISM: Homo sapiens

<400> SEQUENCE: 24 tccoctaggg ccaccacctg ctattctcac aatgg                              35

<210> SEQ ID NO 25
<211> LENGTH: 35
<212> TYPE: DNA
```

<213> ORGANISM: Homo sapiens

<400> SEQUENCE: 25
cagagtgaag cttttccctg ctattctacc aatgg                                    35

<210> SEQ ID NO 26
<211> LENGTH: 40
<212> TYPE: DNA
<213> ORGANISM: Homo sapiens

<400> SEQUENCE: 26
gcggaatgct gtggacagtc tggagtttca cacacgagtt                               40

<210> SEQ ID NO 27
<211> LENGTH: 50
<212> TYPE: DNA
<213> ORGANISM: Homo sapiens

<400> SEQUENCE: 27
cagtggctga gtggacgatg acattcagaa acccatagag ccccggagac                    50

<210> SEQ ID NO 28
<211> LENGTH: 40
<212> TYPE: DNA
<213> ORGANISM: Homo sapiens

<400> SEQUENCE: 28
cgccctcgcc atcgttgggc cagatctgcc cggtcttgcg                               40

<210> SEQ ID NO 29
<211> LENGTH: 35
<212> TYPE: DNA
<213> ORGANISM: Homo sapiens

<400> SEQUENCE: 29
tcagtgcctg gatgtccgtg gccacaccgg acacg                                    35

<210> SEQ ID NO 30
<211> LENGTH: 35
<212> TYPE: DNA
<213> ORGANISM: Homo sapiens

<400> SEQUENCE: 30
cagtggctga gtggacgatg acattcagaa accca                                    35

<210> SEQ ID NO 31
<211> LENGTH: 35
<212> TYPE: DNA
<213> ORGANISM: Homo sapiens

<400> SEQUENCE: 31
gcggaatgct gtggacagtc tggagtttca cacac                                    35

<210> SEQ ID NO 32
<211> LENGTH: 40
<212> TYPE: DNA
<213> ORGANISM: Homo sapiens

<400> SEQUENCE: 32
cgccctcgcc atcgttgggc cagatctgcc cggtcttgcg                               40

<210> SEQ ID NO 33
<211> LENGTH: 50

<212> TYPE: DNA
<213> ORGANISM: Homo sapiens

<400> SEQUENCE: 33
ttcgaggttc tcggggccca tccactgtga ttttgatggc tctgtggtag                50

<210> SEQ ID NO 34
<211> LENGTH: 40
<212> TYPE: DNA
<213> ORGANISM: Homo sapiens

<400> SEQUENCE: 34
cagttactgc cagcagctgt gaaactctca cctccatttc                           40

<210> SEQ ID NO 35
<211> LENGTH: 40
<212> TYPE: DNA
<213> ORGANISM: Homo sapiens

<400> SEQUENCE: 35
cagttactgc cagcagctgt gaaactctca cctccatttc                           40

<210> SEQ ID NO 36
<211> LENGTH: 40
<212> TYPE: DNA
<213> ORGANISM: Homo sapiens

<400> SEQUENCE: 36
cagttactgc cagcagctgt gaaactctca cctccatttc                           40

<210> SEQ ID NO 37
<211> LENGTH: 35
<212> TYPE: DNA
<213> ORGANISM: Homo sapiens

<400> SEQUENCE: 37
taggagtcgg gaggccgaga caggtcaggg agggt                                35

<210> SEQ ID NO 38
<211> LENGTH: 35
<212> TYPE: DNA
<213> ORGANISM: Homo sapiens

<400> SEQUENCE: 38
gccgagacag gtcagggagg gtgcctggct ggctg                                35

<210> SEQ ID NO 39
<211> LENGTH: 35
<212> TYPE: DNA
<213> ORGANISM: Homo sapiens

<400> SEQUENCE: 39
gctgcttttt cttgggctca ctaggagtgg ttttg                                35

<210> SEQ ID NO 40
<211> LENGTH: 35
<212> TYPE: DNA
<213> ORGANISM: Homo sapiens

<400> SEQUENCE: 40
ttttacaggg atacttgggc ggggagccac ttttt                                35

<210> SEQ ID NO 41

```
<211> LENGTH: 35
<212> TYPE: DNA
<213> ORGANISM: Homo sapiens

<400> SEQUENCE: 41
cctgtggact ccatctgctg gaatttttg cttag                              35

<210> SEQ ID NO 42
<211> LENGTH: 35
<212> TYPE: DNA
<213> ORGANISM: Homo sapiens

<400> SEQUENCE: 42
cctgtggact ccatctgctg gaatttttg cttag                              35

<210> SEQ ID NO 43
<211> LENGTH: 35
<212> TYPE: DNA
<213> ORGANISM: Homo sapiens

<400> SEQUENCE: 43
cctgtggact ccatctgctg gaatttttg cttag                              35

<210> SEQ ID NO 44
<211> LENGTH: 35
<212> TYPE: DNA
<213> ORGANISM: Homo sapiens

<400> SEQUENCE: 44
ggcacagaga aagcaaacca ccctgggtgt tatag                             35

<210> SEQ ID NO 45
<211> LENGTH: 35
<212> TYPE: DNA
<213> ORGANISM: Homo sapiens

<400> SEQUENCE: 45
ggcacagaga aagcaaacca ccctgggtgt tatag                             35

<210> SEQ ID NO 46
<211> LENGTH: 41
<212> TYPE: DNA
<213> ORGANISM: Homo sapiens

<400> SEQUENCE: 46
gccacgtggt tgctgttggg caggaagacc tcacttccta t                      41

<210> SEQ ID NO 47
<211> LENGTH: 40
<212> TYPE: DNA
<213> ORGANISM: Homo sapiens

<400> SEQUENCE: 47
gagctgaggt cctgcaggcg caccttgaac tcgtcgaagc                        40

<210> SEQ ID NO 48
<211> LENGTH: 35
<212> TYPE: DNA
<213> ORGANISM: Homo sapiens

<400> SEQUENCE: 48
tggggctagg cggtccatcc aggtggggtg gtgag                             35
```

```
<210> SEQ ID NO 49
<211> LENGTH: 35
<212> TYPE: DNA
<213> ORGANISM: Homo sapiens

<400> SEQUENCE: 49
gcatggcgtg ctcttcaggc ggggagacag agacc                              35

<210> SEQ ID NO 50
<211> LENGTH: 35
<212> TYPE: DNA
<213> ORGANISM: Homo sapiens

<400> SEQUENCE: 50
gcatggcgtg ctcttcaggc ggggagacag agacc                              35

<210> SEQ ID NO 51
<211> LENGTH: 83
<212> TYPE: RNA
<213> ORGANISM: Homo sapiens

<400> SEQUENCE: 51
ucuguggcca acgagccugc gucccaccua gaaucugcug gcuacuacuu gaagauggug   60
aucgcucaca ccaaauccuu gga                                           83

<210> SEQ ID NO 52
<211> LENGTH: 47
<212> TYPE: DNA
<213> ORGANISM: Homo sapiens

<400> SEQUENCE: 52
tccaaggatt tggtgtgagc gatcaccatc ttcaagtagt agccagc                 47

<210> SEQ ID NO 53
<211> LENGTH: 36
<212> TYPE: DNA
<213> ORGANISM: Homo sapiens

<400> SEQUENCE: 53
agattctagg tgggacgcag gctcgttggc cacaga                             36

<210> SEQ ID NO 54
<211> LENGTH: 100
<212> TYPE: RNA
<213> ORGANISM: Homo sapiens

<400> SEQUENCE: 54
cgccggcugu uuaacuucgc uuccgcuggc ccauagugau cuuugcagug acccagcagc   60
aucacuguuu cuuggcgugu gaagauaacc caaggaauug                        100

<210> SEQ ID NO 55
<211> LENGTH: 50
<212> TYPE: DNA
<213> ORGANISM: Homo sapiens

<400> SEQUENCE: 55
caattccttg ggttatcttc acacgccaag aaacagtgat gctgctgggt              50

<210> SEQ ID NO 56
<211> LENGTH: 50
<212> TYPE: DNA
<213> ORGANISM: Homo sapiens
```

```
<400> SEQUENCE: 56
cactgcaaag atcactatgg gccagcggaa gcgaagttaa acagccggcg            50

<210> SEQ ID NO 57
<211> LENGTH: 100
<212> TYPE: RNA
<213> ORGANISM: Homo sapiens

<400> SEQUENCE: 57
cugugauuga cuucaauugc ugacuugugg agaugcagcg aaugugaaau cccacguaua    60
ugccauuucc cucuacgcuc gcugaccguu cuggaagauc                        100

<210> SEQ ID NO 58
<211> LENGTH: 50
<212> TYPE: DNA
<213> ORGANISM: Homo sapiens

<400> SEQUENCE: 58
gatcttccag aacggtcagc gagcgtagag ggaaatggca tatacgtggg             50

<210> SEQ ID NO 59
<211> LENGTH: 50
<212> TYPE: DNA
<213> ORGANISM: Homo sapiens

<400> SEQUENCE: 59
atttcacatt cgctgcatct ccacaagtca gcaattgaag tcaatcacag             50

<210> SEQ ID NO 60
<211> LENGTH: 100
<212> TYPE: RNA
<213> ORGANISM: Homo sapiens

<400> SEQUENCE: 60
cugggagaca gggugaaggg agugguuuuu augaacuuaa cuuagagucu aaaagauuuc    60
uacuggauca cuugucaaga ugcgcccucu cuggggagaa                        100

<210> SEQ ID NO 61
<211> LENGTH: 50
<212> TYPE: DNA
<213> ORGANISM: Homo sapiens

<400> SEQUENCE: 61
ttctccccag agagggcgca tcttgacaag tgatccagta gaaatctttt             50

<210> SEQ ID NO 62
<211> LENGTH: 50
<212> TYPE: DNA
<213> ORGANISM: Homo sapiens

<400> SEQUENCE: 62
agactctaag ttaagttcat aaaaaccact cccttcaccc tgtctcccag             50

<210> SEQ ID NO 63
<211> LENGTH: 100
<212> TYPE: RNA
<213> ORGANISM: Homo sapiens

<400> SEQUENCE: 63
ggaacggcac uguucaccuu uaucugacca aaccgcucua cacgucagca ccaucucugc    60
agcaucucug uaggcucacc auuaacaaau guaccggugc                        100
```

<210> SEQ ID NO 64
<211> LENGTH: 50
<212> TYPE: DNA
<213> ORGANISM: Homo sapiens

<400> SEQUENCE: 64
gcaccggtac atttgttaat ggtgagccta cagagatgct gcagagatgg            50

<210> SEQ ID NO 65
<211> LENGTH: 50
<212> TYPE: DNA
<213> ORGANISM: Homo sapiens

<400> SEQUENCE: 65
tgctgacgtg tagagcggtt tggtcagata aggtgaaca gtgccgttcc             50

<210> SEQ ID NO 66
<211> LENGTH: 100
<212> TYPE: RNA
<213> ORGANISM: Homo sapiens

<400> SEQUENCE: 66
ucagagagca aggcaucggg ggugaaucuu gucuaacauu cccgagguca gccaggcugc    60
uaaccuggaa agcaggaugu aguucugcca ggcaacuuuu                        100

<210> SEQ ID NO 67
<211> LENGTH: 50
<212> TYPE: DNA
<213> ORGANISM: Homo sapiens

<400> SEQUENCE: 67
aaaagttgcc tggcagaact acatcctgct ttccaggtta gcagcctggc             50

<210> SEQ ID NO 68
<211> LENGTH: 50
<212> TYPE: DNA
<213> ORGANISM: Homo sapiens

<400> SEQUENCE: 68
tgacctcggg aatgttagac aagattcacc cccgatgcct tgctctctga             50

<210> SEQ ID NO 69
<211> LENGTH: 100
<212> TYPE: RNA
<213> ORGANISM: Homo sapiens

<400> SEQUENCE: 69
aaauggaaaa ccaggacgcc cuggucugca uaucugagag cguuccagag ccgaucgugg    60
aaugggugcu uugcgauuca caggggggaaa gcuguaaaga                       100

<210> SEQ ID NO 70
<211> LENGTH: 50
<212> TYPE: DNA
<213> ORGANISM: Homo sapiens

<400> SEQUENCE: 70
tctttacagc tttccccctg tgaatcgcaa agcacccatt ccacgatcgg             50

<210> SEQ ID NO 71
<211> LENGTH: 50
<212> TYPE: DNA

<213> ORGANISM: Homo sapiens

<400> SEQUENCE: 71
ctctggaacg ctctcagata tgcagaccag ggcgtcctgg tttttccattt      50

<210> SEQ ID NO 72
<211> LENGTH: 100
<212> TYPE: RNA
<213> ORGANISM: Homo sapiens

<400> SEQUENCE: 72
aagaaucaca aagaacugug ucaacuagca gagaguccaa gcagaagggc agauggacuu      60 cuucagliguguc cuucacggca cuggauccca ucaaagaacc      100

<210> SEQ ID NO 73
<211> LENGTH: 50
<212> TYPE: DNA
<213> ORGANISM: Homo sapiens

<400> SEQUENCE: 73
ggttctttga tgggatccag tgccgtgaag gacactgaag aagtccatct      50

<210> SEQ ID NO 74
<211> LENGTH: 50
<212> TYPE: DNA
<213> ORGANISM: Homo sapiens

<400> SEQUENCE: 74
gcccttctgc ttggactctc tgctagttga cacagttctt tgtgattctt      50

<210> SEQ ID NO 75
<211> LENGTH: 86
<212> TYPE: RNA
<213> ORGANISM: Homo sapiens

<400> SEQUENCE: 75
ggucuuugau gagugugggga ucacggauga ucagcuccuu gcccuccugc cuucccugag      60
ccacugcucc cagcuuacaa ccuuaa      86

<210> SEQ ID NO 76
<211> LENGTH: 43
<212> TYPE: DNA
<213> ORGANISM: Homo sapiens

<400> SEQUENCE: 76
ttaaggttgt aagctgggag cagtggctca gggaaggcag gag      43

<210> SEQ ID NO 77
<211> LENGTH: 43
<212> TYPE: DNA
<213> ORGANISM: Homo sapiens

<400> SEQUENCE: 77
ggcaaggagc tgatcatccg tgatcccaca ctcatcaaag acc      43

<210> SEQ ID NO 78
<211> LENGTH: 100
<212> TYPE: RNA
<213> ORGANISM: Homo sapiens

<400> SEQUENCE: 78
ggaauaggac uagguuuauu uacccauugu gagggluagag aggcgagucu ggaggagcag      60
ggauugggag aagggguggaa aaaauacucu gauucuuaaa                    100

<210> SEQ ID NO 79
<211> LENGTH: 50
<212> TYPE: DNA
<213> ORGANISM: Homo sapiens

<400> SEQUENCE: 79
tttaagaatc agagtatttt tccaccccct ctcccaatcc ctgctcctcc          50

<210> SEQ ID NO 80
<211> LENGTH: 50
<212> TYPE: DNA
<213> ORGANISM: Homo sapiens

<400> SEQUENCE: 80
agactcgcct ctctaccctc acaatgggta aataaaccta gtcctattcc          50

<210> SEQ ID NO 81
<211> LENGTH: 100
<212> TYPE: RNA
<213> ORGANISM: Homo sapiens

<400> SEQUENCE: 81
gaccucauca uuaugugggg gcuuuguucu ccacaggguc agguaagaga uggccuucuu   60
ggcugccaca aucagaaauc acgcaggcau uuugggguagg                    100

<210> SEQ ID NO 82
<211> LENGTH: 50
<212> TYPE: DNA
<213> ORGANISM: Homo sapiens

<400> SEQUENCE: 82
cctacccaaa atgcctgcgt gatttctgat tgtggcagcc aagaaggcca          50

<210> SEQ ID NO 83
<211> LENGTH: 50
<212> TYPE: DNA
<213> ORGANISM: Homo sapiens

<400> SEQUENCE: 83
tctcttacct gaccctgtgg agaacaaagc ccccacataa tgatgaggtc          50

<210> SEQ ID NO 84
<211> LENGTH: 88
<212> TYPE: RNA
<213> ORGANISM: Homo sapiens

<400> SEQUENCE: 84
agggugacga accaaggagc cgucgacucg cuggaauaca auuacccggg cgaggcgccc   60
ucgggacauu uugacauguu uucgcccu                                  88

<210> SEQ ID NO 85
<211> LENGTH: 43
<212> TYPE: DNA
<213> ORGANISM: Homo sapiens

<400> SEQUENCE: 85
agggcgaaaa catgtcaaaa tgtcccgagg gcgcctcgcc cgg                 43

<210> SEQ ID NO 86

```
<211> LENGTH: 45
<212> TYPE: DNA
<213> ORGANISM: Homo sapiens

<400> SEQUENCE: 86
gtaattgtat tccagcgagt cgacggctcc ttggttcgtc accct              45

<210> SEQ ID NO 87
<211> LENGTH: 100
<212> TYPE: RNA
<213> ORGANISM: Homo sapiens

<400> SEQUENCE: 87
uugaaaccgg uagggaguga uaauccgcau ucaguugucg aggagugcca gucaccuuca   60
guuucuggag cuggccguca acauguccuu uccuaaggcg                         100

<210> SEQ ID NO 88
<211> LENGTH: 50
<212> TYPE: DNA
<213> ORGANISM: Homo sapiens

<400> SEQUENCE: 88
cgccttagga aggacatgt tgacggccag ctccagaaac tgaaggtgac            50

<210> SEQ ID NO 89
<211> LENGTH: 50
<212> TYPE: DNA
<213> ORGANISM: Homo sapiens

<400> SEQUENCE: 89
tggcactcct cgacaactga atgcggatta tcactcccta ccggtttcaa          50

<210> SEQ ID NO 90
<211> LENGTH: 100
<212> TYPE: RNA
<213> ORGANISM: Homo sapiens

<400> SEQUENCE: 90
accacacauc ccagcccaau ccagguacgc acagacaggu uuucacauaa augcagccca   60
uuucuccaga acccauuuga gggguggggg gguguuaauu                         100

<210> SEQ ID NO 91
<211> LENGTH: 50
<212> TYPE: DNA
<213> ORGANISM: Homo sapiens

<400> SEQUENCE: 91
aattaacacc cccccacccc tcaaatgggt tctggagaaa tgggctgcat          50

<210> SEQ ID NO 92
<211> LENGTH: 50
<212> TYPE: DNA
<213> ORGANISM: Homo sapiens

<400> SEQUENCE: 92
ttatgtgaaa acctgtctgt gcgtacctgg attgggctgg gatgtgtggt          50

<210> SEQ ID NO 93
<211> LENGTH: 78
<212> TYPE: RNA
<213> ORGANISM: Homo sapiens

<400> SEQUENCE: 93
```

```
gcggcgcucg ccaagucccu caaaaugacg gacgcgcagg ucaagaccug guuccaaaac    60
cggaggacca aguggcgg                                                  78

<210> SEQ ID NO 94
<211> LENGTH: 40
<212> TYPE: DNA
<213> ORGANISM: Homo sapiens

<400> SEQUENCE: 94
ccgccacttg gtcctccggt tttggaacca ggtcttgacc                          40

<210> SEQ ID NO 95
<211> LENGTH: 38
<212> TYPE: DNA
<213> ORGANISM: Homo sapiens

<400> SEQUENCE: 95
tgcgcgtccg tcattttgag ggacttggcg agcgccgc                            38

<210> SEQ ID NO 96
<211> LENGTH: 100
<212> TYPE: RNA
<213> ORGANISM: Homo sapiens

<400> SEQUENCE: 96
ggggcaggac uaggaauaug gaccaaaagg aagaucgaag uaggugaaaa guugggccu     60 uaugugggag agcagagguc aaaccugaaa gaccccaguu                         100

<210> SEQ ID NO 97
<211> LENGTH: 50
<212> TYPE: DNA
<213> ORGANISM: Homo sapiens

<400> SEQUENCE: 97
aactggggtc tttcaggttt gacctctgct ctcccacata aggcccaaac               50

<210> SEQ ID NO 98
<211> LENGTH: 50
<212> TYPE: DNA
<213> ORGANISM: Homo sapiens

<400> SEQUENCE: 98
ttttcaccta cttcgatctt cctttggtc catattccta gtcctgcccc                50

<210> SEQ ID NO 99
<211> LENGTH: 99
<212> TYPE: RNA
<213> ORGANISM: Homo sapiens

<400> SEQUENCE: 99
cccugguccu gacuucccug gaggagaagu auuccuguug cugucuucag ucucacagag    60
aagcuccugc uacuucccca gcucucagua guuuaguac                           99

<210> SEQ ID NO 100
<211> LENGTH: 50
<212> TYPE: DNA
<213> ORGANISM: Homo sapiens

<400> SEQUENCE: 100
gtactaaact actgagagct ggggaagtag caggagcttc tctgtgagac                50
```

```
<210> SEQ ID NO 101
<211> LENGTH: 49
<212> TYPE: DNA
<213> ORGANISM: Homo sapiens

<400> SEQUENCE: 101
tgaagacagc aacaggaata cttctcctcc agggaagtca ggaccaggg              49

<210> SEQ ID NO 102
<211> LENGTH: 100
<212> TYPE: RNA
<213> ORGANISM: Homo sapiens

<400> SEQUENCE: 102
ccuaucuccg gcuaaauaca cuuugugaac gccuucuguc ugagcaccca gaauuagaac  60
auaucaucug gacccuuuuc cagcacaccc ugcagaauga                       100

<210> SEQ ID NO 103
<211> LENGTH: 50
<212> TYPE: DNA
<213> ORGANISM: Homo sapiens

<400> SEQUENCE: 103
tcattctgca gggtgtgctg aaaagggtc cagatgatat gttctaattc              50

<210> SEQ ID NO 104
<211> LENGTH: 50
<212> TYPE: DNA
<213> ORGANISM: Homo sapiens

<400> SEQUENCE: 104
tgggtgctca gacagaaggc gttcacaaag tgtatttagc cggagatagg             50

<210> SEQ ID NO 105
<211> LENGTH: 94
<212> TYPE: RNA
<213> ORGANISM: Homo sapiens

<400> SEQUENCE: 105
cagggcucac uccagccacc ugaaguccaa aaagggucag ucuaccuccc gccauaaaaa  60
acucauguuc aagacagaag ggccugacuc agac                             94

<210> SEQ ID NO 106
<211> LENGTH: 50
<212> TYPE: DNA
<213> ORGANISM: Homo sapiens

<400> SEQUENCE: 106
gtctgagtca ggcccttctg tcttgaacat gagttttta tggcgggagg              50

<210> SEQ ID NO 107
<211> LENGTH: 44
<212> TYPE: DNA
<213> ORGANISM: Homo sapiens

<400> SEQUENCE: 107
tagactgacc cttttggac ttcaggtggc tggagtgagc cctg                    44

<210> SEQ ID NO 108
<211> LENGTH: 74
<212> TYPE: RNA
<213> ORGANISM: Homo sapiens
```

<400> SEQUENCE: 108
gagguggggc ugcagcacuu ccucagcuuu cugagcucca ugcgccgccc uaucuuggcc    60
ugcuacaagc ugug                                                     74

<210> SEQ ID NO 109
<211> LENGTH: 39
<212> TYPE: DNA
<213> ORGANISM: Homo sapiens

<400> SEQUENCE: 109
cacagcttgt agcaggccaa gatagggcgg cgcatggag                           39

<210> SEQ ID NO 110
<211> LENGTH: 35
<212> TYPE: DNA
<213> ORGANISM: Homo sapiens

<400> SEQUENCE: 110
ctcagaaagc tgaggaagtg ctgcagcccc acctc                              35

<210> SEQ ID NO 111
<211> LENGTH: 76
<212> TYPE: RNA
<213> ORGANISM: Homo sapiens

<400> SEQUENCE: 111
cuggggccca ucuaggagug gcaucuuuuu uggugcccug aaggccagcu cuggaccuuc    60
ccaggaaaag ugccag                                                   76

<210> SEQ ID NO 112
<211> LENGTH: 36
<212> TYPE: DNA
<213> ORGANISM: Homo sapiens

<400> SEQUENCE: 112
ctggcacttt tcctgggaag gtccagagct ggcctt                             36

<210> SEQ ID NO 113
<211> LENGTH: 40
<212> TYPE: DNA
<213> ORGANISM: Homo sapiens

<400> SEQUENCE: 113
cagggcacca aaaagatgc cactcctaga tgggcccag                            40

<210> SEQ ID NO 114
<211> LENGTH: 96
<212> TYPE: RNA
<213> ORGANISM: Homo sapiens

<400> SEQUENCE: 114
cagccaugaa gaaccagguu gcaagauuua augaccucag guuugucggu cgaaguggaa    60
gagggaaaag cuucacucug accaucacug ucuuca                             96

<210> SEQ ID NO 115
<211> LENGTH: 46
<212> TYPE: DNA
<213> ORGANISM: Homo sapiens

<400> SEQUENCE: 115
tgaagacagt gatggtcaga gtgaagcttt tccctcttcc acttcg                        46

<210> SEQ ID NO 116
<211> LENGTH: 50
<212> TYPE: DNA
<213> ORGANISM: Homo sapiens

<400> SEQUENCE: 116
accgacaaac ctgaggtcat taaatcttgc aacctggttc ttcatggctg                    50

<210> SEQ ID NO 117
<211> LENGTH: 91
<212> TYPE: RNA
<213> ORGANISM: Homo sapiens

<400> SEQUENCE: 117
cgccacuacu acaaacuaaa cauuaucagg aaggagccag gacaaaggcu uuguucagg          60 uuuaugaaaa ccccagauga aaucaugagu g                                        91

<210> SEQ ID NO 118
<211> LENGTH: 50
<212> TYPE: DNA
<213> ORGANISM: Homo sapiens

<400> SEQUENCE: 118
cactcatgat ttcatctggg gttttcataa acctgaacaa agcctttgt                     50

<210> SEQ ID NO 119
<211> LENGTH: 41
<212> TYPE: DNA
<213> ORGANISM: Homo sapiens

<400> SEQUENCE: 119
cctggctcct tcctgataat gtttagtttg tagtagtggc g                             41

<210> SEQ ID NO 120
<211> LENGTH: 73
<212> TYPE: RNA
<213> ORGANISM: Homo sapiens

<400> SEQUENCE: 120
cuuggagcag caagugcgag agcggaaccu gaaucccaaa gcagccuguu ugaaacggcg         60
agaagaggaa aag                                                            73

<210> SEQ ID NO 121
<211> LENGTH: 38
<212> TYPE: DNA
<213> ORGANISM: Homo sapiens

<400> SEQUENCE: 121
cttttcctct tctcgccgtt tcaaacaggc tgctttgg                                 38

<210> SEQ ID NO 122
<211> LENGTH: 35
<212> TYPE: DNA
<213> ORGANISM: Homo sapiens

<400> SEQUENCE: 122
gattcaggtt ccgctctcgc acttgctgct ccaag                                    35

<210> SEQ ID NO 123
<211> LENGTH: 100

```
<212> TYPE: RNA
<213> ORGANISM: Homo sapiens

<400> SEQUENCE: 123
cgggaggaag caggacauug gagacauuuu acagcaaauu augaccauca cagaccagag    60
uuuggaugag gcgcaggcca gaaaacaugc uuuaaacugc                        100

<210> SEQ ID NO 124
<211> LENGTH: 50
<212> TYPE: DNA
<213> ORGANISM: Homo sapiens

<400> SEQUENCE: 124
gcagtttaaa gcatgttttc tggcctgcgc ctcatccaaa ctctggtctg              50

<210> SEQ ID NO 125
<211> LENGTH: 50
<212> TYPE: DNA
<213> ORGANISM: Homo sapiens

<400> SEQUENCE: 125
tgatggtcat aatttgctgt aaaatgtctc caatgtcctg cttcctcccg              50

<210> SEQ ID NO 126
<211> LENGTH: 71
<212> TYPE: RNA
<213> ORGANISM: Homo sapiens

<400> SEQUENCE: 126 caguuugcc caggcuggc ucgaacuccu ggcaucaagc gauccuccug ccuuagccuc    60
ccagaguacu g                                                       71

<210> SEQ ID NO 127
<211> LENGTH: 36
<212> TYPE: DNA
<213> ORGANISM: Homo sapiens

<400> SEQUENCE: 127
cagtactctg ggaggctaag gcaggaggat cgcttg                            36

<210> SEQ ID NO 128
<211> LENGTH: 35
<212> TYPE: DNA
<213> ORGANISM: Homo sapiens

<400> SEQUENCE: 128
atgccaggag ttcgagacca gcctgggcaa cactg                             35

<210> SEQ ID NO 129
<211> LENGTH: 100
<212> TYPE: RNA
<213> ORGANISM: Homo sapiens

<400> SEQUENCE: 129
cugcuagaaa aaucacgggc aauucgccaa gccagagacg agaggacauu ccacaucuuu    60
uacuacauga uugcuggagc caaggagaag augagaagug                        100

<210> SEQ ID NO 130
<211> LENGTH: 50
<212> TYPE: DNA
<213> ORGANISM: Homo sapiens
```

```
<400> SEQUENCE: 130
cacttctcat cttctccttg gctccagcaa tcatgtagta aaagatgtgg              50

<210> SEQ ID NO 131
<211> LENGTH: 50
<212> TYPE: DNA
<213> ORGANISM: Homo sapiens

<400> SEQUENCE: 131
aatgtcctct cgtctctggc ttggcgaatt gcccgtgatt tttctagcag              50

<210> SEQ ID NO 132
<211> LENGTH: 98
<212> TYPE: RNA
<213> ORGANISM: Homo sapiens

<400> SEQUENCE: 132
caaaaugagu ggacacaugu aaauugugcu uuguggucag cggaaguguu ugaagaugau   60
gacggaucac uaaagaaugu gcauauggcu gugaucag                          98

<210> SEQ ID NO 133
<211> LENGTH: 48
<212> TYPE: DNA
<213> ORGANISM: Homo sapiens

<400> SEQUENCE: 133
ctgatcacag ccatatgcac attctttagt gatccgtcat catcttca                48

<210> SEQ ID NO 134
<211> LENGTH: 50
<212> TYPE: DNA
<213> ORGANISM: Homo sapiens

<400> SEQUENCE: 134
aacacttccg ctgaccacaa agcacaattt acatgtgtcc actcattttg              50

<210> SEQ ID NO 135
<211> LENGTH: 100
<212> TYPE: RNA
<213> ORGANISM: Homo sapiens

<400> SEQUENCE: 135
ugaacugaaa ccacugccgg aggacuaucg acagcagacc uuugaaaaaa cagacuugaa   60
agugccugcc aaagccaagc ucaccaaacu gaagaugccu                        100

<210> SEQ ID NO 136
<211> LENGTH: 50
<212> TYPE: DNA
<213> ORGANISM: Homo sapiens

<400> SEQUENCE: 136
aggcatcttc agtttggtga gcttggcttt ggcaggcact ttcaagtctg              50

<210> SEQ ID NO 137
<211> LENGTH: 50
<212> TYPE: DNA
<213> ORGANISM: Homo sapiens

<400> SEQUENCE: 137 tttttttcaaa ggtctgctgt cgatagtcct ccggcagtgg tttcagttca             50
```

<210> SEQ ID NO 138
<211> LENGTH: 75
<212> TYPE: RNA
<213> ORGANISM: Homo sapiens

<400> SEQUENCE: 138
aacucgugug ugaaacucca gacuguccac agcauccgc ugaccaucaa uaaggaagaa    60
gcccuucagc ggcca                                                   75

<210> SEQ ID NO 139
<211> LENGTH: 35
<212> TYPE: DNA
<213> ORGANISM: Homo sapiens

<400> SEQUENCE: 139
tggccgctga agggcttctt ccttattgat ggtca                              35

<210> SEQ ID NO 140
<211> LENGTH: 40
<212> TYPE: DNA
<213> ORGANISM: Homo sapiens

<400> SEQUENCE: 140
gcggaatgct gtggacagtc tggagtttca cacacgagtt                         40

<210> SEQ ID NO 141
<211> LENGTH: 85
<212> TYPE: RNA
<213> ORGANISM: Homo sapiens

<400> SEQUENCE: 141
gucuccgggg cucuaugggu uucugaaugu caucguccac ucagccacug gauuuaagca   60
gaguucaaaa gcccuucagc ggcca                                        85

<210> SEQ ID NO 142
<211> LENGTH: 35
<212> TYPE: DNA
<213> ORGANISM: Homo sapiens

<400> SEQUENCE: 142
tggccgctga agggcttttg aactctgctt aaatc                              35

<210> SEQ ID NO 143
<211> LENGTH: 50
<212> TYPE: DNA
<213> ORGANISM: Homo sapiens

<400> SEQUENCE: 143
cagtggctga gtggacgatg acattcagaa acccatagag ccccggagac              50

<210> SEQ ID NO 144
<211> LENGTH: 75
<212> TYPE: RNA
<213> ORGANISM: Homo sapiens

<400> SEQUENCE: 144
cgcaagaccg ggcagaucug gcccaacgau ggcgagggcg ccuuccaugg agacgcagaa   60
gcccuucagc ggcca                                                   75

<210> SEQ ID NO 145
<211> LENGTH: 35
<212> TYPE: DNA

```
<213> ORGANISM: Homo sapiens

<400> SEQUENCE: 145
tggccgctga agggcttctg catctccatg gaagg                              35

<210> SEQ ID NO 146
<211> LENGTH: 40
<212> TYPE: DNA
<213> ORGANISM: Homo sapiens

<400> SEQUENCE: 146
cgccctcgcc atcgttgggc cagatctgcc cggtcttgcg                         40

<210> SEQ ID NO 147
<211> LENGTH: 70
<212> TYPE: RNA
<213> ORGANISM: Homo sapiens

<400> SEQUENCE: 147
cguguccggu guggccacgg acauccaggc acugaaggca gccuucgacg ucaaagcccu   60
ucagcggcca                                                         70

<210> SEQ ID NO 148
<211> LENGTH: 35
<212> TYPE: DNA
<213> ORGANISM: Homo sapiens

<400> SEQUENCE: 148
tggccgctga agggctttga cgtcgaaagc tgcct                              35

<210> SEQ ID NO 149
<211> LENGTH: 35
<212> TYPE: DNA
<213> ORGANISM: Homo sapiens

<400> SEQUENCE: 149
tcagtgcctg gatgtccgtg gccacaccgg acacg                              35

<210> SEQ ID NO 150
<211> LENGTH: 70
<212> TYPE: RNA
<213> ORGANISM: Homo sapiens

<400> SEQUENCE: 150
uggguuucug aaugucaucg uccacucagc cacuggauuu aagcagaguu caagugaaaa   60
gcuccggguc                                                         70

<210> SEQ ID NO 151
<211> LENGTH: 35
<212> TYPE: DNA
<213> ORGANISM: Homo sapiens

<400> SEQUENCE: 151
gacccggagc ttttcacttg aactctgctt aaatc                              35

<210> SEQ ID NO 152
<211> LENGTH: 35
<212> TYPE: DNA
<213> ORGANISM: Homo sapiens

<400> SEQUENCE: 152
cagtggctga gtggacgatg acattcagaa accca                              35
```

<210> SEQ ID NO 153
<211> LENGTH: 70
<212> TYPE: RNA
<213> ORGANISM: Homo sapiens

<400> SEQUENCE: 153
gugugugaaa cuccagacug uccacagcau uccgcugacc aucaauaagg aaggugaaaa    60 gcuccgggüc                                                          70

<210> SEQ ID NO 154
<211> LENGTH: 35
<212> TYPE: DNA
<213> ORGANISM: Homo sapiens

<400> SEQUENCE: 154
gacccggagc ttttcacctt ccttattgat ggtca                              35

<210> SEQ ID NO 155
<211> LENGTH: 35
<212> TYPE: DNA
<213> ORGANISM: Homo sapiens

<400> SEQUENCE: 155
gcggaatgct gtggacagtc tggagtttca cacac                              35

<210> SEQ ID NO 156
<211> LENGTH: 75
<212> TYPE: RNA
<213> ORGANISM: Homo sapiens

<400> SEQUENCE: 156
cgcaagaccg ggcagaucug gcccaacgau ggcgagggcg ccuuccaugg agacgcaggu    60
gaaaagcucc ggguc                                                    75

<210> SEQ ID NO 157
<211> LENGTH: 35
<212> TYPE: DNA
<213> ORGANISM: Homo sapiens

<400> SEQUENCE: 157
gacccggagc ttttcacctg catctccatg gaagg                              35

<210> SEQ ID NO 158
<211> LENGTH: 40
<212> TYPE: DNA
<213> ORGANISM: Homo sapiens

<400> SEQUENCE: 158
cgccctcgcc atcgttgggc cagatctgcc cggtcttgcg                          40

<210> SEQ ID NO 159
<211> LENGTH: 100
<212> TYPE: RNA
<213> ORGANISM: Homo sapiens

<400> SEQUENCE: 159
cuaccacaga gccaucaaaa ucacagugga ugggccccga gaaccucgaa aucguacuga    60
gaagcacucc acaaugccag acucaccugu ggaugugaag                        100

<210> SEQ ID NO 160

<211> LENGTH: 50
<212> TYPE: DNA
<213> ORGANISM: Homo sapiens

<400> SEQUENCE: 160
cttcacatcc acaggtgagt ctggcattgt ggagtgcttc tcagtacgat         50

<210> SEQ ID NO 161
<211> LENGTH: 50
<212> TYPE: DNA
<213> ORGANISM: Homo sapiens

<400> SEQUENCE: 161
ttcgaggttc tcggggccca tccactgtga ttttgatggc tctgtggtag         50

<210> SEQ ID NO 162
<211> LENGTH: 75
<212> TYPE: RNA
<213> ORGANISM: Homo sapiens

<400> SEQUENCE: 162
gaaauggagg ugagaguuuc acagcugcug gcaguaacug guccaugagc uggagaaguc     60
caagcgggcc cugga                                              75

<210> SEQ ID NO 163
<211> LENGTH: 35
<212> TYPE: DNA
<213> ORGANISM: Homo sapiens

<400> SEQUENCE: 163
tccagggccc gcttggactt ctccagctca tggac                        35

<210> SEQ ID NO 164
<211> LENGTH: 40
<212> TYPE: DNA
<213> ORGANISM: Homo sapiens

<400> SEQUENCE: 164
cagttactgc cagcagctgt gaaactctca cctccatttc                   40

<210> SEQ ID NO 165
<211> LENGTH: 80
<212> TYPE: RNA
<213> ORGANISM: Homo sapiens

<400> SEQUENCE: 165
gaaauggagg ugagaguuuc acagcugcug gcaguaacug aaugaaguug agagcgucac     60
agggaugcuu aacgaggccg                                         80

<210> SEQ ID NO 166
<211> LENGTH: 40
<212> TYPE: DNA
<213> ORGANISM: Homo sapiens

<400> SEQUENCE: 166
cggcctcgtt aagcatccct gtgacgctct caacttcatt                   40

<210> SEQ ID NO 167
<211> LENGTH: 40
<212> TYPE: DNA
<213> ORGANISM: Homo sapiens

<400> SEQUENCE: 167
cagttactgc cagcagctgt gaaactctca cctccatttc                                40

<210> SEQ ID NO 168
<211> LENGTH: 75
<212> TYPE: RNA
<213> ORGANISM: Homo sapiens

<400> SEQUENCE: 168
gaaauggagg ugagaguuuc acagcugcug gcaguaacug gccaaggcga accuagacaa         60
gaauaagcag acgcu                                                          75

<210> SEQ ID NO 169
<211> LENGTH: 35
<212> TYPE: DNA
<213> ORGANISM: Homo sapiens

<400> SEQUENCE: 169
agcgtctgct tattcttgtc taggttcgcc ttggc                                    35

<210> SEQ ID NO 170
<211> LENGTH: 40
<212> TYPE: DNA
<213> ORGANISM: Homo sapiens

<400> SEQUENCE: 170
cagttactgc cagcagctgt gaaactctca cctccatttc                               40

<210> SEQ ID NO 171
<211> LENGTH: 70
<212> TYPE: RNA
<213> ORGANISM: Homo sapiens

<400> SEQUENCE: 171
acccucccug accugucucg gccucccgac uccuacagug augaaagugu ucggucaccu         60
ggaaccuuuu                                                                70

<210> SEQ ID NO 172
<211> LENGTH: 35
<212> TYPE: DNA
<213> ORGANISM: Homo sapiens

<400> SEQUENCE: 172
aaaaggttcc aggtgaccga acactttcat cactg                                    35

<210> SEQ ID NO 173
<211> LENGTH: 35
<212> TYPE: DNA
<213> ORGANISM: Homo sapiens

<400> SEQUENCE: 173
taggagtcgg gaggccgaga caggtcaggg agggt                                    35

<210> SEQ ID NO 174
<211> LENGTH: 69
<212> TYPE: RNA
<213> ORGANISM: Homo sapiens

<400> SEQUENCE: 174
agccagccag gcacccuccc ugaccugucu cggccucccg acuccuacag uguuuugagu         60
auccgagga                                                                 69

<210> SEQ ID NO 175
<211> LENGTH: 35
<212> TYPE: DNA
<213> ORGANISM: Homo sapiens

<400> SEQUENCE: 175
tcctcggata ctcaaaacac tgtaggagtc gggag                      35

<210> SEQ ID NO 176
<211> LENGTH: 35
<212> TYPE: DNA
<213> ORGANISM: Homo sapiens

<400> SEQUENCE: 176
gccgagacag gtcagggagg gtgcctggct ggctg                      35

<210> SEQ ID NO 177
<211> LENGTH: 70
<212> TYPE: RNA
<213> ORGANISM: Homo sapiens

<400> SEQUENCE: 177
caaaaccacu ccuagugagc ccaagaaaaa gcagccucca ccaccagaau cagaacaaua      60
ugauacaucu                                                            70

<210> SEQ ID NO 178
<211> LENGTH: 35
<212> TYPE: DNA
<213> ORGANISM: Homo sapiens

<400> SEQUENCE: 178
agatgtatca tattgttctg attctggtgg tggag                      35

<210> SEQ ID NO 179
<211> LENGTH: 35
<212> TYPE: DNA
<213> ORGANISM: Homo sapiens

<400> SEQUENCE: 179
gctgcttttt cttgggctca ctaggagtgg ttttg                      35

<210> SEQ ID NO 180
<211> LENGTH: 70
<212> TYPE: RNA
<213> ORGANISM: Homo sapiens

<400> SEQUENCE: 180
aaaaaguggc uccccgccca aguaucccug uaaaacaaaa accaaaagaa aaggaaauga      60
cccauucaug                                                            70

<210> SEQ ID NO 181
<211> LENGTH: 35
<212> TYPE: DNA
<213> ORGANISM: Homo sapiens

<400> SEQUENCE: 181
catgaatggg tcatttcctt ttcttttggt ttttg                      35

<210> SEQ ID NO 182
<211> LENGTH: 35
<212> TYPE: DNA
<213> ORGANISM: Homo sapiens

<400> SEQUENCE: 182
ttttacaggg atacttgggc ggggagccac tttttt          35

<210> SEQ ID NO 183
<211> LENGTH: 70
<212> TYPE: RNA
<213> ORGANISM: Homo sapiens

<400> SEQUENCE: 183
aaaaaguggc uccccgccca aguaucccug uaaaacaaaa accaaaagaa aagcagaccu          60
acuccaauga                                                                70

<210> SEQ ID NO 184
<211> LENGTH: 35
<212> TYPE: DNA
<213> ORGANISM: Homo sapiens

<400> SEQUENCE: 184
tcattggagt aggtctgctt ttcttttggt ttttg          35

<210> SEQ ID NO 185
<211> LENGTH: 35
<212> TYPE: DNA
<213> ORGANISM: Homo sapiens

<400> SEQUENCE: 185
ttttacaggg atacttgggc ggggagccac tttttt          35

<210> SEQ ID NO 186
<211> LENGTH: 70
<212> TYPE: RNA
<213> ORGANISM: Homo sapiens

<400> SEQUENCE: 186
cuaagcaaaa aauuccagca gauggagucc acaggaucag aguggacuuu aaggaaauga          60
cccauucaug                                                                70

<210> SEQ ID NO 187
<211> LENGTH: 35
<212> TYPE: DNA
<213> ORGANISM: Homo sapiens

<400> SEQUENCE: 187
catgaatggg tcatttcctt aaagtccact ctgat          35

<210> SEQ ID NO 188
<211> LENGTH: 36
<212> TYPE: DNA
<213> ORGANISM: Homo sapiens

<400> SEQUENCE: 188
cctgtggact ccatctgctg gaattttttg cttagc          36

<210> SEQ ID NO 189
<211> LENGTH: 70
<212> TYPE: RNA
<213> ORGANISM: Homo sapiens

<400> SEQUENCE: 189
cuaagcaaaa aauuccagca gauggagucc acaggaucag aguggacuuu aagcagaccu          60
acuccaauga                                                                                70

<210> SEQ ID NO 190
<211> LENGTH: 35
<212> TYPE: DNA
<213> ORGANISM: Homo sapiens

<400> SEQUENCE: 190
tcattggagt aggtctgctt aaagtccact ctgat                                    35

<210> SEQ ID NO 191
<211> LENGTH: 35
<212> TYPE: DNA
<213> ORGANISM: Homo sapiens

<400> SEQUENCE: 191
cctgtggact ccatctgctg gaattttttg cttag                                    35

<210> SEQ ID NO 192
<211> LENGTH: 70
<212> TYPE: RNA
<213> ORGANISM: Homo sapiens

<400> SEQUENCE: 192
cuauaacacc cagggugguu ugcuuucucu gugccaguag ugggcaugua gaggaaauga         60
cccauucaug                                                                70

<210> SEQ ID NO 193
<211> LENGTH: 35
<212> TYPE: DNA
<213> ORGANISM: Homo sapiens

<400> SEQUENCE: 193
catgaatggg tcatttccta tacatgccca ctact                                    35

<210> SEQ ID NO 194
<211> LENGTH: 35
<212> TYPE: DNA
<213> ORGANISM: Homo sapiens

<400> SEQUENCE: 194
ggcacagaga aagcaaacca ccctgggtgt tatag                                    35

<210> SEQ ID NO 195
<211> LENGTH: 70
<212> TYPE: RNA
<213> ORGANISM: Homo sapiens

<400> SEQUENCE: 195
cuauaacacc cagggugguu ugcuuucucu gugccaguag ugggcaugua gagcagaccu         60
acuccaauga                                                                70

<210> SEQ ID NO 196
<211> LENGTH: 35
<212> TYPE: DNA
<213> ORGANISM: Homo sapiens

<400> SEQUENCE: 196
tcattggagt aggtctgcta tacatgccca ctact                                    35

<210> SEQ ID NO 197
<211> LENGTH: 35

```
<212> TYPE: DNA
<213> ORGANISM: Homo sapiens

<400> SEQUENCE: 197
ggcacagaga aagcaaacca ccctgggtgt tatag                              35

<210> SEQ ID NO 198
<211> LENGTH: 76
<212> TYPE: RNA
<213> ORGANISM: Homo sapiens

<400> SEQUENCE: 198
auaggaagug aggucuuccu gcccaacagc aaccacgugg ccaguggcgc cggggaggca   60
gccauugaga cccaga                                                  76

<210> SEQ ID NO 199
<211> LENGTH: 35
<212> TYPE: DNA
<213> ORGANISM: Homo sapiens

<400> SEQUENCE: 199
tctgggtctc aatggctgac tcccaagcgc cactg                             35

<210> SEQ ID NO 200
<211> LENGTH: 41
<212> TYPE: DNA
<213> ORGANISM: Homo sapiens

<400> SEQUENCE: 200
gccacgtggt tgctgttggg caggaagacc tcacttccta t                      41

<210> SEQ ID NO 201
<211> LENGTH: 76
<212> TYPE: RNA
<213> ORGANISM: Homo sapiens

<400> SEQUENCE: 201
ggcuucgacg aguucaaggu gcgccugcag gaccucagcu cuugcaucac ccaggggaaa   60
gccauugaga cccaga                                                  76

<210> SEQ ID NO 202
<211> LENGTH: 35
<212> TYPE: DNA
<213> ORGANISM: Homo sapiens

<400> SEQUENCE: 202
tctgggtctc aatggctttc cactgggtga tgcaa                             35

<210> SEQ ID NO 203
<211> LENGTH: 40
<212> TYPE: DNA
<213> ORGANISM: Homo sapiens

<400> SEQUENCE: 203
gagctgaggt cctgcaggcg caccttgaac tcgtcgaagc                        40

<210> SEQ ID NO 204
<211> LENGTH: 70
<212> TYPE: RNA
<213> ORGANISM: Homo sapiens

<400> SEQUENCE: 204
```

-continued

```
cucaccaccc caccuggaug gaccgccuag ccccaggagc cccgucauag gaaccauuga    60
gacccagagc                                                           70
```

<210> SEQ ID NO 205
<211> LENGTH: 35
<212> TYPE: DNA
<213> ORGANISM: Homo sapiens

<400> SEQUENCE: 205

```
gctctgggtc tcaatggttc ctatgacggg actcc                               35
```

<210> SEQ ID NO 206
<211> LENGTH: 35
<212> TYPE: DNA
<213> ORGANISM: Homo sapiens

<400> SEQUENCE: 206

```
tggggctagg cggtccatcc aggtggggtg gtgag                               35
```

<210> SEQ ID NO 207
<211> LENGTH: 70
<212> TYPE: RNA
<213> ORGANISM: Homo sapiens

<400> SEQUENCE: 207

```
ggucucuguc uccccgccug aagagcacgc caugcccauu gggagaauag cagguggugg    60
cccuagggga                                                           70
```

<210> SEQ ID NO 208
<211> LENGTH: 35
<212> TYPE: DNA
<213> ORGANISM: Homo sapiens

<400> SEQUENCE: 208

```
tcccctaggg ccaccacctg ctattctcac aatgg                               35
```

<210> SEQ ID NO 209
<211> LENGTH: 35
<212> TYPE: DNA
<213> ORGANISM: Homo sapiens

<400> SEQUENCE: 209

```
gcatggcgtg ctcttcaggc ggggagacag agacc                               35
```

<210> SEQ ID NO 210
<211> LENGTH: 70
<212> TYPE: RNA
<213> ORGANISM: Homo sapiens

<400> SEQUENCE: 210

```
ggucucuguc uccccgccug aagagcacgc caugcccauu gggagaauag cagggaaaag    60
cuucacucug                                                           70
```

<210> SEQ ID NO 211
<211> LENGTH: 35
<212> TYPE: DNA
<213> ORGANISM: Homo sapiens

<400> SEQUENCE: 211

```
cagagtgaag cttttccctg ctattctacc aatgg                               35
```

```
<210> SEQ ID NO 212
<211> LENGTH: 35
<212> TYPE: DNA
<213> ORGANISM: Homo sapiens

<400> SEQUENCE: 212
gcatggcgtg ctcttcaggc ggggagacag agacc                            35
```